US011001868B2

(12) United States Patent
Kvam et al.

(10) Patent No.: US 11,001,868 B2
(45) Date of Patent: May 11, 2021

(54) CELL-FREE PROTEIN EXPRESSION USING DOUBLE-STRANDED CONCATAMERIC DNA

(71) Applicant: Global Life Sciences Solutions Operations UK Ltd, Sheffield (GB)

(72) Inventors: Erik Leeming Kvam, Schenectady, NY (US); John Richard Nelson, Clifton park, NY (US); Wei Gao, Clifton Park, NY (US)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 551 days.

(21) Appl. No.: 15/631,510

(22) Filed: Aug. 11, 2017

(65) Prior Publication Data

US 2019/0048379 A1    Feb. 14, 2019

(51) Int. Cl.
*C12P 21/00* (2006.01)
*C12P 19/34* (2006.01)
*C12P 21/02* (2006.01)

(52) U.S. Cl.
CPC ............... *C12P 21/00* (2013.01); *C12P 19/34* (2013.01); *C12P 21/02* (2013.01)

(58) Field of Classification Search
CPC .................................. C12P 21/00; C12P 19/34
See application file for complete search history.

(56) References Cited

U.S. PATENT DOCUMENTS

| 8,226,976 B2 | 7/2012 | Yokoyama et al. | |
| 8,715,732 B2 | 5/2014 | Luo et al. | |
| 2004/0142356 A1* | 7/2004 | Patterson | C12N 9/0069 435/6.13 |
| 2005/0260653 A1* | 11/2005 | Labaer | C07K 1/047 435/6.12 |
| 2009/0042740 A1 | 2/2009 | Ji | |
| 2016/0097050 A1 | 4/2016 | Greenleaf et al. | |

FOREIGN PATENT DOCUMENTS

| WO | 2016034849 A1 | 3/2016 |
| WO | 2017191007 A1 | 11/2017 |

OTHER PUBLICATIONS

Hadi et al.; Rolling circle amplification of synthetic DNA accelerates biocatalytic determination of enzyme activity relative to conventional methods; Scientific Reports, 10:10279, pp. 1-8 (2020) (Year: 2020).*
Kumar et al., "Cell-free Protein Synthesis using Multiply-Primed Rolling Circle Amplification Products", Biotechniques, vol. 47, Issue 1, pp. 637-639, Jul. 2009.
Rosenblum et al., "Engine out of the Chassis: Cell-Free Protein Synthesis and its Uses", FEBS Letter, vol. 588, Issue 2, pp. 261-268, Jan. 21, 2014.
Abe et al., "Rolling Circle Translation of Circular RNA in Living Human Cells", Scientific Reports, vol. 5, Article No. 16435, 2015.
Gagoski et al., "Gateway-Compatible Vectors for High-Throughput Protein Expression in Pro- and Eukaryotic Cell-Free Systems", Journal of Biotechnology, vol. 195, pp. 1-7, Feb. 10, 2015.
Naoke, Abe et al: "Rolling Circle Translation of Circular RNA in Living Human Cells", Scientific Reports, vol. 5, No. 1. Nov. 10, 2015.
Gyanendra, Kumar et al. "Cell-Free Protein Synthesis Using Multiply-Primed Rolling Circle Amplification Products", Biotechniques Rapid Dispatches, vol. 47, No. 1, Jul. 1, 2009, pp. 637-639.
International Search Report and Written Opinion for corresponding PCT application No. PCT/EP2018/071229 dated Oct. 15, 2018; 15 pages.

* cited by examiner

*Primary Examiner* — Antonio Galisteo Gonzalez
(74) *Attorney, Agent, or Firm* — Eversheds Sutherland (US) LLP

(57) ABSTRACT

Methods for in vitro transcription and translation using a double-stranded concatemeric DNA in a eukaryotic cell-free expression system are provided. The method includes the steps of (a) contacting a double-stranded concatemeric DNA with a eukaryotic cell-free expression system, and (b) expressing a protein in vitro from the double-stranded concatemeric DNA in the eukaryotic cell-free expression system. The double-stranded concatemeric DNA includes a plurality of tandem repeat sequences. The plurality of tandem repeat sequences includes an expression sequence including a promoter, a cap-independent translation element (CITE), and an open reading frame. A final concentration of the double-stranded concatemeric DNA in the eukaryotic cell-free expression system is in a range from about 0.1 ng/µL to about 35 ng/µL. A RCA product DNA may be used as the double stranded concatemer DNA for the methods.

27 Claims, 6 Drawing Sheets

Specification includes a Sequence Listing.

SEQUENCE LISTING

<160> NUMBER OF SEQ ID NOS: 9

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: May or may not be present

<400> SEQUENCE: 1

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: May or may not be present

<400> SEQUENCE: 2

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: May or may not be present

<400> SEQUENCE: 3

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: May or may not be present

<400> SEQUENCE: 4

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 5
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ccgggatccc agtgaattgt aatacgactc actatagggc gaattaattc cggttatttt      60
ccaccatatt gccgtctttt ggcaatgtga gggcccggaa acctggccct gtcttcttga     120
cgagcattcc tagggtctt tcccctctcg ccaaaggaat gcaaggtctg ttgaatgtcg      180
tgaaggaagc agttcctctg gaagcttctt gaagacaaaa acgtctgta gcgacccttt     240 gcaggcagcg gaacccccca cctggcgaca ggtgcctctg cggccaaaag ccacgtgtat     300
aagatacacc tgcaaaggcg gcacaacccc agtgccacgt tgtgagttgg atagttgtgg    360
aaagagtcaa atggctcacc tcaagcgtat tcaacaaggg gctgaaggat gcccagaagg    420 tacccccattg tatgggatct gatctggggc ctcggtgcac atgctttaca tgtgtttagt    480
cgaggttaaa aaacgtctag gccccccgaa ccacggggac gtggttttcc tttgaaaaac    540
acgatgataa tatggccaca accgtgagca agggcgagga gctgttcacc ggggtggtgc    600
ccatcctggt cgagctggac ggcgacgtaa acggccacaa gttcagcgtg tccggcgagg    660
gtgaaggcga cgctacttac ggaaagctga cactgaagtt catttgcacc acaggcaaac    720
tgcctgtgcc ctggccaacc ctcgtgacta ccctcacata cggcgtgcag tgctttagca    780
gatatcctga tcatatgaaa cagcacgact tctttaagtc tgctatgcct gaaggatacg    840
tgcaggagag aaccatcttc ttcaaggacg acggaaacta taagactaga gccgaggtga    900
agtttgaggg agacacactg gtgaatagga tcgagctgaa gggcattgac ttcaaggagg    960
acggaaacat cctgggccac aagctggagt acaactacaa tagccacaac gtctatatta   1020
tggctgataa gcaagagaac ggaatcaagg tgaacttcaa gatcagacac aacatcgagg   1080
acggcagcgt gcagctggcc gaccactacc agcagaatac ccctatcgga cggccccg    1140 tgctcctgcc agacaaccac tacctgagca cccagtccgc cctgagcaaa gaccccaacg    1200
agaagcgcga tcatatggtt ctgctggagt tcgtgaccgc cgccggcatc actcttggta    1260
tggacgagct gtacaagtaa taagatctga ctgaaaaaaa aaaagtttaa acactagtcc    1320
gctgagcaat aactagcata accccttggg gcctctaaac gggtcttgag gggttttttg   1380
ctgcagagat ctccg                                                     1395

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base

```
<222> LOCATION: (1)..(2)
<223> OTHER INFORMATION: A, C, G, or T/U
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(5)
<223> OTHER INFORMATION: 2-amino dA, 2-thio dT, normal G or normal C
<220> FEATURE:
<221> NAME/KEY: misc_feature
<222> LOCATION: (5)..(6)
<223> OTHER INFORMATION: Phosphorothioate linkage between nucleotides
<220> FEATURE:
<221> NAME/KEY: modified_base
<222> LOCATION: (6)..(6)
<223> OTHER INFORMATION: A, C, G, or T/U

<400> SEQUENCE: 6 nnnnnn                                                                    6

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-biotin
<220> FEATURE:
<221> NAME/KEY: modified_base
<222> LOCATION: (1)..(6)
<223> OTHER INFORMATION: A, C, G, or T/U
<220> FEATURE:
<221> NAME/KEY: misc_feature
<222> LOCATION: (4)..(6)
<223> OTHER INFORMATION: Phosphorothioate linkage between nucleotides

<400> SEQUENCE: 7 nnnnnn                                                                    6

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Tyr Lys Asp Asp Asp Asp Lys
1               5
```

CELL-FREE PROTEIN EXPRESSION USING DOUBLE-STRANDED CONCATAMERIC DNA

SEQUENCE LISTING

The instant application contains a Sequence Listing, which has been submitted electronically in ASCII format and is hereby incorporated by reference in its entirety. Said ASCII copy, created on Jun. 16, 2017, is named 316478-1_SL.txt and is 5,663 bytes in size.

FIELD OF INVENTION

The invention generally relates to improved cell-free protein expression systems that involve in vitro transcription and translation (IVTT) of a double-stranded concatemeric DNA.

BACKGROUND

Cell-free protein expression provides a simple and efficient method for generating proteins without the complications of cell culture, cell engineering, or cell transfection. Cell-free protein expression systems for expressing recombinant proteins address various limitations of cell-based expression systems such as protein toxicity, protein degradation, protein aggregation and misfolding, uncontrolled post-translational modification, or negative effects of protein expression on cell growth due to sequestration of cellular machinery. Significantly higher quantities of proteins can be expressed in a shorter period using a cell-free protein expression system that can be employed for downstream high-throughput structural and functional analyses. Such in vitro protein expression also has significant advantages in terms of cost savings, streamlined production, easier scale-up, and simplified purification. In a cell-free protein expression system, a desired protein of interest is expressed by adding a deoxyribonucleic acid (DNA) or ribonucleic acid (RNA) that encodes a gene of the protein of interest to a transcription-translation-competent cellular extract, and performing the transcription and/or translation of the gene of interest. The transcription and translation of the DNA containing the gene of interest may be coupled in a single reaction to enable immediate translation of a newly synthesized mRNA into protein or it may be linked wherein an mRNA is generated in a first reaction followed by translation of the generated mRNA into protein in a second reaction. The coupled in vitro transcription and translation (coupled transcription-translation in a cell-free system) generally increases the yield of expressed proteins with less time and in vitro manipulation. The immediate translation of the mRNA also avoids possible adverse effects associated with mRNA degradation or misfolding.

One limitation of in vitro transcription-translation systems is that it requires larger quantities (generally in microgram quantities) of a DNA template. Generally, sufficient amounts of such DNA templates can only be obtained through multiple workflow steps and significant labor. For example, suitable DNA templates for IVTT may be generated by synthesizing a DNA template from multiple polymerase chain reactions (PCR) and/or cloning the DNA template into a plasmid vector and propagating the plasmid vector in a host cell such as E. coli. However, PCR is often not amenable for large-scale generation of high-quality DNA, due in part to the high mutation rate of PCR. Additionally, thermal cycling of PCR reactions is difficult to scale-up to larger reactions due to limitations on how quickly temperatures can be ramped in large volumes. Moreover, PCR products, being linear DNA sequences, is rapidly degraded by the nucleases present in cell-free transcription-translation extracts. Further, sub-cloning of a gene of interest into a plasmid vector followed by high-scale propagation in E. coli through genetic selection is time-consuming and labor intensive.

In general, cell-free transcription and translation in a mammalian cell-free extract is not as efficient as the one using prokaryotic cell extract. One common method for enhancing protein expression using mammalian cell-free extract is to supply reagents in excess (e.g. amino acids and energy sources) and use a dialysis membrane to remove waste products that adversely affect the translation. However, in a dialysis process, the volume of the IVTT reaction increases significantly. Further, the template DNA may not be recoverable from the dialysis chamber. Thus, the template DNA must be provided in substantially higher amounts to maintain the required final concentration of the template DNA for efficient IVTT when dialysis is being employed.

Isothermal DNA amplification techniques such as rolling circle amplification (RCA) can be employed to generate large quantities of high-quality DNA with less effort, time, and expense. Isothermal amplification reactions render scale-up to larger reaction sizes straight forward as there is no requirement for rapid heating and cooling. Rolling circle amplification employs a circular DNA template and generates RCA products that are tandem repeat units (concatemers) of the template DNA. RCA of a plasmid DNA, followed by coupled in vitro transcription and translation, is possible to generate the protein of interest. However, these plasmids are generally created via standard cloning methods involving genetic-selection inside a host cell such as E. coli. Such plasmids contain many additional coding and non-coding sequences including sequences for the origin of replication (e.g., oriC), antibiotic selection (e.g., amp for beta-lactamase), and accessory sequences that are used for selection and/or screening plasmids (e.g., lacZ, beta-galactosidase) in the host cells. Transcription and/or expression of these ancillary sequences are not desired and may make the entire workflow inefficient.

There exists a need for improved in vitro transcription and translation eukaryotic systems for easy generation of desired proteins form limited concentration of template DNA compared to plasmid DNA and thus does not require PCR-based template DNA synthesis. Also, it is desirable to enable cell-free protein systems using methods that are simple, cost-effective, and less time-consuming.

BRIEF DESCRIPTION

In some embodiments, a method for in vitro transcription and translation using a double-stranded concatemeric DNA is provided. The method includes the steps of (a) contacting a double-stranded concatemeric DNA with a eukaryotic cell-free expression system, and (b) expressing a protein in vitro from the double-stranded concatemeric DNA in the eukaryotic cell-free expression system. The double-stranded concatemeric DNA includes a plurality of tandem repeat sequences, wherein each of the plurality of tandem repeat sequences includes an expression sequence. The expression sequence includes a promoter, a cap-independent translation element (CITE), and an open reading frame (ORF). A final concentration of the double-stranded concatemeric DNA in the eukaryotic cell-free expression system is in a range from about 0.1 ng/μL to about 35 ng/μL.

In some embodiments, a method for in vitro transcription and translation using and double-stranded concatemeric (DNA) generated from a DNA mini-circle is provided. The method comprises the steps of (a) providing a DNA mini-circle, (b) generating a double-stranded concatemeric DNA via rolling circle amplification of the DNA mini-circle, and (c) contacting the generated double-stranded concatemeric DNA with a eukaryotic cell-free expression system in vitro to express a protein from the double-stranded concatemeric DNA via transcription and translation. The final concentration of the double-stranded concatemeric DNA in the eukaryotic cell-free expression system is in a range from about 0.1 ng/μL to 35 ng/μL.

DRAWINGS

These and other features, aspects and advantages of the invention will become better understood when the following detailed description is read with reference to the accompanying figures.

Figure 6A:
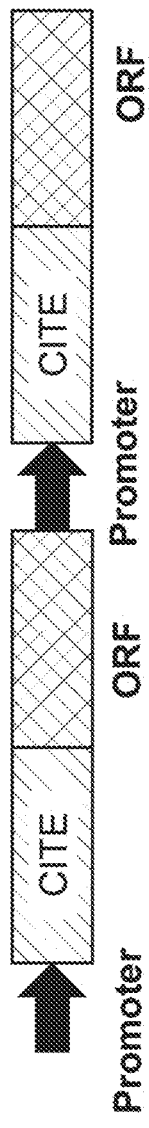
Figure 6B:
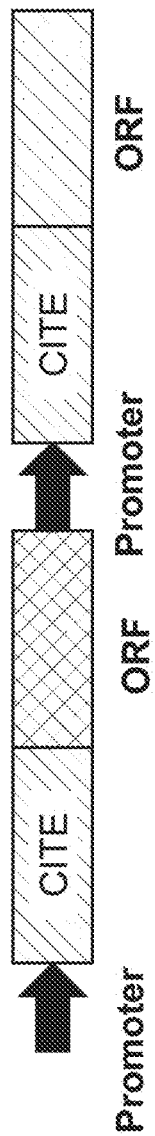
Figure 6C:
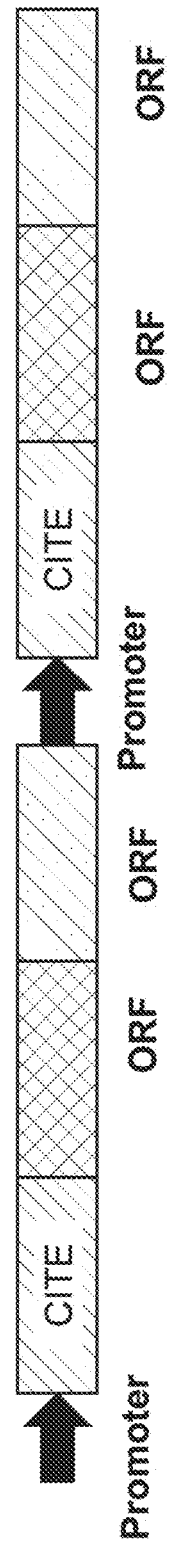

FIG. 6A-C are schematic representations of tandem repeat sequences including two expression sequences, wherein the expression sequences code for a same protein (FIG. 6A), the expression sequences code for two different proteins (FIG. 6B), or each of the expression sequences includes two ORFs that code two different proteins (FIG. 6C).

DETAILED DESCRIPTION

The following detailed description is exemplary and not intended to limit the invention or uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Where necessary, ranges have been supplied and those ranges are inclusive of all sub-ranges there between. To more clearly and concisely describe and point out the subject matter of the claimed invention, the following definitions are provided for specific terms, which are used in the following description and the appended claims.

As used herein, the term "nucleoside" refers to a glycosylamine compound wherein a nucleic acid base (nucleobase) is linked to a sugar moiety. A "nucleotide" refers to a nucleoside phosphate. A nucleotide may be represented using alphabetical letters (letter designation) corresponding to its nucleoside as described in Table 1. For example, A denotes adenosine (a nucleoside containing the nucleobase, adenine), C denotes cytidine, G denotes guanosine, U denotes uridine, and T denotes thymidine (5-methyl uridine). N represents a random nucleoside, and dNTP refers to deoxyribonucleoside triphosphate. N may be any of A, C, G, or T/U.

TABLE 1

Letter designations of various nucleotides.

| Symbol Letter | Nucleotide represented by the symbol Letter |
|---|---|
| G | G |
| A | A |
| T | T |
| C | C |
| U | U |
| N | G or A or T/U or C |

As used herein, the term "nucleotide analogue" refers to compounds that are structurally analogous to naturally occurring nucleotides. The nucleotide analogue may have an altered phosphate backbone, sugar moiety, nucleobase, or combinations thereof. Nucleotide analogues may be a natural nucleotide, a synthetic nucleotide, a modified nucleotide, or a surrogate replacement moiety (e.g., inosine). Generally, nucleotide analogues with altered nucleobases confer, among other things, different base pairing and base stacking proprieties. As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at the 2' position and 4' position (e.g., 2'-C, 4'-C-oxymethylene linkage; see, for example, Singh, S. K., et. al., Chem. Comm., 4, 455-456, 1998, or Koshkin, A. A., et. al., Tetrahedron, 54, 3607-3630, 1998.)). The 2' and 4' position of the furanose unit in the LNA nucleotide may be linked by an O-methylene (e.g., oxy-LNA: 2'-O, 4'-C-methylene-β-D-ribofuranosyl nucleotide), an S-methylene (thio-LNA), or an NH-methylene moiety (amino-LNA), and the like. Such linkages restrict the conformational freedom of the furanose ring. LNA oligonucleotides display enhanced hybridization affinity toward complementary single-stranded RNA, and complementary single- or double-stranded DNA. The LNA oligonucleotides may induce A-type (RNA-like) duplex conformations. PNA's backbone is composed of repeating N-(2-aminoethyl)-glycine units linked by peptide bonds. The various purine and pyrimidine bases are linked to the backbone by a methylene bridge (—$CH_2$—) and a carbonyl group (—(C=O)—). PNAs are depicted like peptides, with the N-terminus at the first (left) position and the C-terminus at the last (right) position. PNA oligomers show greater specificity in binding to complementary DNAs, the binding efficiency and specificity also applies to PNA/RNA duplexes. PNAs are not easily recognized by either nucleases or proteases, making them resistant to degradation by enzymes. PNAs are also stable over a wide pH range. Nucleotide analogues having altered phosphate-sugar backbone (e.g., PNA, LNA) often modify, among other things, the chain properties such as secondary structure formation. A star (*) sign preceding a letter designation denotes that the nucleotide designated by the letter is a phosphorothioate modified nucleotide. For example, *N represents a phosphorothioate modified random nucleotide, "atN" represents a random nucleotide, wherein the nucleotide may be any of 2-amino dA, 2-thio-dT, normal G or normal C, A plus (+) sign preceding a letter designation denotes that the nucleotide designated by the letter is a LNA nucleotide. For example, +A represents an adenosine LNA nucleotide, and +N represents a locked random nucleotide (i.e., a random LNA nucleotide).

As used herein, the term "modified nucleotides" refers to nucleotides having modifications, wherein an additional moiety is attached the nucleotides (e.g., a biotinylated nucleotide). The modifications may either face the major groove or minor groove. Modified nucleotides are a convenient tool for the enzymatic introduction of functional groups into a nucleic acid target of interest. The modification to the major groove of the nucleobase allow better incorporation efficiency with the 5-position of pyrimidines and the 7-position of purines. Often the required modifications are introduced to a nucleotide through a linker (e.g., a biotin moiety attached a nucleotide via a linker). The flexibility of the linker arm attaching to the modification site can influence nucleotide utilization. For example, rigid linear linkers provide better dNTP incorporation while nucleic acid amplification. Linker arm length also plays a role in incorporation of modified dNTPs during amplification. For example, biotinylated nucleotides are often prepared by conjugation of 5-aminoallyl-dCTP and 5-aminoallyl-dUTP with a biotin-containing linker to prepare biotinylated nucleotides. The linker position and length also affect the introduction of functional groups for each of the four dNTPs. Modified dNTPs with shorter linker arms are better substrates for amplification reaction than nucleotides with longer linker arms.

As used herein, the term "oligonucleotide" refers to oligomers of nucleotides. The term "nucleic acid" as used herein refers to polymers of nucleotides. The term "sequence" as used herein refers to a nucleotide sequence of an oligonucleotide or a nucleic acid. Throughout the specification, whenever an oligonucleotide or nucleic acid is represented by a sequence of letters, the nucleotides are in 5'→3' order from left to right. The oligonucleotides or nucleic acids may be a DNA, an RNA, or their analogues (e.g., phosphorothioate analogue). The oligonucleotides or nucleic acids may also include modified bases and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof.

As used herein, the term "primer" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long.

As used herein, the term "random primer" refers to a mixture of primer sequences, generated by randomizing a nucleotide at any given location in an oligonucleotide sequence in such a way that the given location may consist of any of the possible nucleotides or their analogues (complete randomization). Thus, the random primer is a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for performing a whole-genome amplification reaction. Random primers may also be effective in priming and producing double-stranded rolling circle amplification (RCA) product rather than single-stranded RCA product, depending on the concentration of primer.

As used herein, the term "rolling circle amplification (RCA)" refers to a nucleic acid amplification reaction that amplifies a circular nucleic acid template (e.g., single/double stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single, specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential amplification kinetics featuring a cascade in series of multiple-hybridization, primer-extension, and strand-displacement events involving both the primers and both strands. This often generates a discrete set of concatemeric, double-stranded nucleic acid amplification products. The RCA may be performed in vitro under isothermal conditions using a suitable nucleic acid polymerase such as Phi29 DNA polymerase. Suitable polymerases possess strand displacement DNA synthesis ability.

As used herein the term "expression sequence" refers to a DNA sequence that is competent for protein expression. In other words, an expression sequence is an expression competent unit that includes at least one promoter operably linked to one or more open reading frames (ORF). The one or more ORFs may code for one or more same or different proteins. In some instances, an expression sequence may include one promoter operably linked to more than one ORFs. For example, an expression sequence may include a promoter functionally linked to two different ORFs, one encoding a heavy chain, and the other encoding a light chain of an antibody. An expression sequence may further include sequences such as cap-independent translation element (CITE) for aiding efficient protein expression.

One or more embodiments are directed to methods for expressing a protein in a eukaryotic cell-free expression system (e.g., an in vitro transcription and translation system or IVTT). In one embodiment, the protein is expressed by in vitro transcription and translation of a double-stranded concatemeric DNA (e.g., a RCA product DNA that is generated by rolling circle amplification). These in vitro transcription and translation reactions yield proteins products that are devoid of any contamination of intact cells. Generation of such proteins may be desired in a myriad of applications including structural and functional proteomics. The cell-free expression of such proteins may be particularly desirable for therapeutic applications.

Cell-free expression generally encompasses two modes: (1) mRNA and protein are made in a single reaction (e.g., a coupled IVTT) and (2) mRNA is made in a first reaction and the resulting mRNA product is added to a second, separate translation reaction (e.g., a linked IVTT). The double-stranded concatemeric DNA such as a double-stranded-RCA product DNA may be utilized for either modes, (1) or (2). For example, in one embodiment, the RCA product may be provided to a coupled in vitro transcription-translation reaction, wherein the RCA product DNA is converted to an mRNA and the mRNA is simultaneously expressed to a protein in a single reaction mixture that is capable of producing RNA and protein. In another embodiment, the RCA product may be provided to a linked transcription-translation reaction, wherein the RCA product DNA is first converted to mRNA in a transcription reaction mixture, and the generated mRNA is then added to a translation reaction mixture for protein express. In some embodiments, the RCA products provided to the coupled in vitro transcription-translation reaction or linked transcription-translation reaction are derived from a DNA mini-circle.

Figure 1:
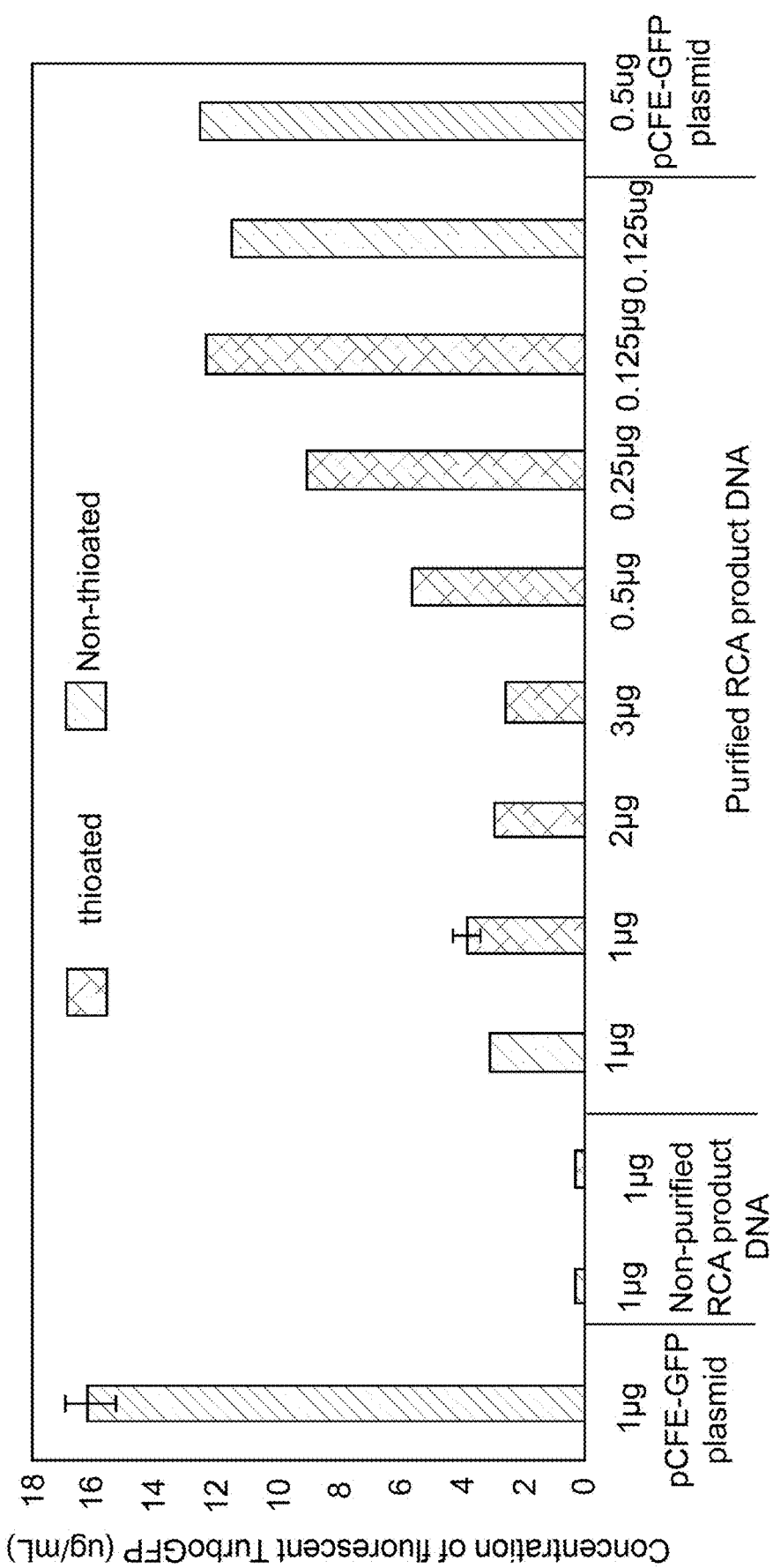
FIG. 1 illustrates cell-free expression of an Turbo green fluorescent protein (TurboGFP) using different concentrations of thioated or non-thioated RCA product DNA, generated from a plasmid DNA, as a template for in vitro transcription and translation as compared to a non-amplified plasmid DNA.
Figure 2:
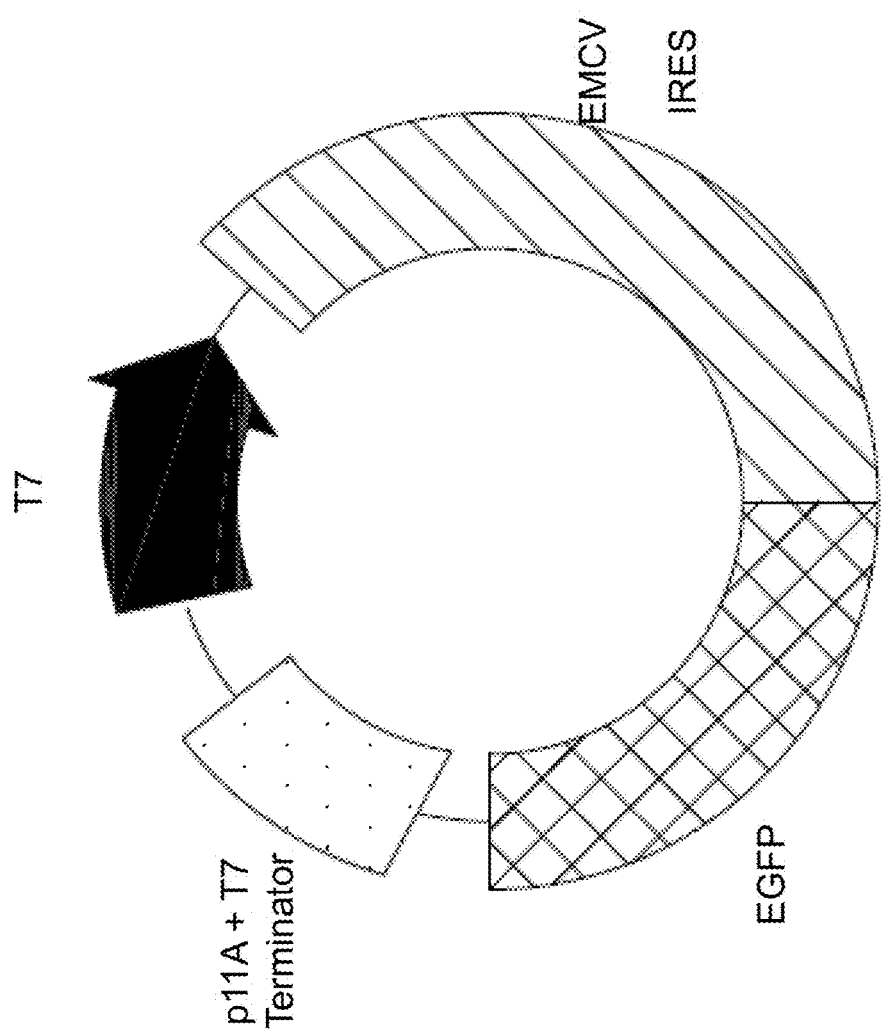
FIG. 2 illustrates a DNA mini-circle having a minimalistic expression sequence.

In one embodiment, the method for in vitro transcription and translation includes the steps of contacting a double-stranded concatemeric DNA with a eukaryotic cell-free expression system and expressing a protein in vitro from the double-stranded concatemeric DNA in the eukaryotic cell-free expression system. The double-stranded concatemeric DNA comprises a plurality of tandem repeat sequences. Each of the plurality of tandem repeat sequences comprises an expression sequence comprising a promoter, a cap-independent translation element (CITE), and an ORF. A final concentration of the double-stranded concatemeric DNA in the eukaryotic cell-free expression system is in a range from about 0.1 ng/μL to about 35 ng/μL. FIGS. 1, and 3-5 illustrate the cell-free expression of different proteins using different concentrations of double-stranded concatemeric DNA as template for in vitro transcription and translation reactions. In some embodiments, the double-stranded concatemeric DNA is a double-stranded rolling circle amplification (RCA) product. In some embodiments, the RCA product DNA is derived from a minimalistic expression sequence. One embodiment of the minimalistic expression sequence (mini-circle) is shown in FIG. 2. FIG. 2 illustrates a minimalistic expression sequence comprising a transcription terminator (p11A+T7 terminator) including a polyA sequence p11A, wherein p11A represents 11 adenine residues.

In some embodiments, each of the plurality of tandem repeat sequences comprises at least one expression sequence. In such embodiments, the at least one expression sequence comprises at least one promoter, at least one CITE, and at least one ORF. In some embodiments, each of the plurality of tandem repeat sequences comprises two or more expression sequences. The two or more expression sequences may code for a same protein or different proteins. In some embodiments, the expression sequence includes at least one promoter that is functionally linked to at least one ORF. For example, in one aspect, in an expression sequence one promoter is functionally linked to one ORF as schematically illustrated in FIG. 6A and FIG. 6B. In another aspect, in an expression sequence, one promoter is functionally linked to two different ORFs as schematically illustrated in FIG. 6C. In some embodiments, the expression sequence may include two or more promoters functionally linked to two or more ORFs.

Referring further to FIGS. 6A-C, FIG. 6A illustrates a tandem repeat sequence including two expression sequences, wherein both expression sequences code for same protein. In another example, FIG. 6B illustrates a tandem repeat sequence including two expression sequences, wherein a first expression sequence codes for a first protein and a second expression sequence code for a second protein, the first protein being different from the second protein. In both FIG. 6A and FIG. 6B, the illustrated expression sequence includes a promoter functionally linked to a cap-independent translation element (e.g., IRES) and a single ORF.

FIG. 6C illustrates an expression sequence including two ORFs that code two different proteins. In FIG. 6C, an expression sequence includes a promoter operably linked to two different ORFs, each of them coding a protein that is different from the other. In this example, a single promoter is functionally linked to two ORFs via a cap-independent translation element. Each of the ORFs includes translation start and translation stop sequences. Having a translational termination or stop sequence is required, otherwise an infinite polyprotein may be synthesized, which is undesirable. However, a transcriptional stop codon may be optional for the first ORF leading to the generation of a polycistronic mRNA upon transcription. In such instances, the intervening sequences between the first and second ORFs may be selected such that upon IVTT even if a single polycistronic mRNA is produced, it can be translated to two different proteins.

In FIG. 6C, one promoter is functionally coupled to an IRES and two ORFs (e.g., a first ORF and a second ORF).

The first ORF codes for a first protein and the second ORF codes for a second protein, different from the first protein. Each of the ORFs includes translation start and translation stop sequences. A polycistronic mRNA gets generated upon transcription of the expression sequence illustrated in FIG. 6C. Synthesis of the first protein by translation of the first ORF may be followed by a ribosomal slippage to the second translation start sequence of the second ORF to initiate the synthesis of the second protein from the second ORF. This may be achieved by incorporating "self-cleaving sequences" between the first and second ORFs. Suitable self-cleaving sequences such as viral P2A motif facilitates the creation of two or more proteins from one single mRNA.

As noted above, in absence of an IRES element, "self-cleaving" 2A peptides may be incorporated into the muliti-cistronic sequence to produce equimolar levels of multiple genes from the same mRNA upon translation. These 2A peptides typically function by making the ribosome skip the synthesis of a peptide bond at the C-terminus of a 2A element leading to a separation between the end of the 2A sequence and the start of the next downstream peptide. The "cleavage" occurs between the Glycine and Proline residues found on the C-terminus meaning the upstream cistron will have a few additional residues added to the end, while the downstream cistron will start with the Proline. Four different 2A peptides, such as SEQ. ID. No. 1-4, are commonly used (Table 2) for self-cleavage purpose in eukaryotic cells.

TABLE 2

Representative 2A Peptide sequences

| SEQ. ID. No. | Peptide | Amino acid sequence |
|---|---|---|
| 1 | T2A | (GSG) EGRGSLLTCGDVEENPGP |
| 2 | P2A | (GSG) ATNFSLLKQAGDVEENPGP |
| 3 | E2A | (GSG) QCTNYALLKLAGDVESNPGP |
| 4 | F2A | (GSG) VKQTLNFDLLKLAGDVESNPGP |

In one or more embodiments, the double-stranded concatemeric DNA is a double-stranded RCA product DNA. The RCA product DNA may be a linear or a branched concatemer having tandem repeat sequences. In some embodiments, multiple (e.g., two) separate double stranded concatemeric DNA may be employed, wherein each of the separate double stranded concatemeric DNA includes expression sequences encoding different proteins. For example, two RCA product DNAs may be employed, wherein a first RCA product DNA includes a first expression sequence encoding a first protein and a second RCA product DNA includes a second expression sequence encoding a second protein, wherein the first protein is different from the second protein. The double-stranded concatemeric DNA such as RCA product DNA, may comprise a modified nucleotide, a nucleotide analogue, or a combination thereof.

In some embodiments, the double stranded concatemeric DNA comprises a nucleotide analogue (e.g., a phosphorothioated nucleotide) or a modified nucleotide (e.g., a biotinylated nucleotide). The double-stranded concatemeric DNA may include, but is not limited to, a biotinylated nucleotide, a phosphorothioated nucleotide, an inosine-containing nucleotide, a LNA nucleotide, a PNA nucleotide, 2-amino-deoxyadenosine, 2-thio-deoxythymidine, a polycation nucleotide or a combination thereof. In some embodiments, each of the tandem repeat sequences of the double stranded concatemeric DNA comprises a nucleotide analogue.

In some embodiments, the double stranded concatemeric DNA comprises a phosphorothioated nucleotide. The phosphorothioated nucleotides include phosphorothioated dNTPs, such as α-S-dATP or α-S-dTTP. The term "phosphorothioated" nucleotide is interchangeably used hereinafter as a "thioated" nucleotide. In some embodiments, the double-stranded concatemeric DNA, such as an RCA product DNA, may be internally thioated (have alpha-thio-dNTP). In some embodiments, to generate a double-stranded concatemeric DNA that are internally thioated, RCA reactions are supplemented with phosphorothioated nucleotides. The phosphorothioated nucleotides are incorporated into the dNTP mixture for random incorporation of thioated bases into the RCA product DNA during amplification. In some other embodiments, an RCA product DNA comprising a phosphorothioated nucleotide may be generated (e.g., thioated, having alpha-thio-dNTP) by employing a thioated primer sequence for the RCA reaction. In certain embodiments, the double-stranded concatemeric DNA comprises a biotinylated nucleotide, which may be used for conjugating the double-stranded concatemeric DNA to a substrate such as a streptavidin-attached bead. A biotinylated double-stranded concatemeric DNA may be generated by performing an RCA reaction using a biotinylated primer. The resulting biotinylated RCA product DNA is generally purified to remove excess biotinylated primers prior to conjugation to the streptavidin-attached bead. The purified biotinylated RCA product DNA may be mixed with streptavidin beads to conjugate the RCA product DNA onto the streptavidin beads.

Conventionally, for an IVTT reaction using a prokaryotic cell-free expression system, such as one using an *E. coli* cell lysate, 5-10 ng of template DNA is required per microliter of IVTT reaction. For a IVTT reaction using a protozoal cell lysate, at least 35 ng/μL of plasmid DNA was needed for adequate protein expression. However, for IVTT reaction using a eukaryotic or mammalian cell lysate, such as HeLa or CHO cell lysate, more than 40 ng/μL of plasmid DNA has been conventionally used for higher cell-free protein expression yield. Generation of such large quantities of plasmid DNA for eukaryotic IVTT reaction is often labor-intensive and not cost-effective. In contrast, efficiency of a eukaryotic cell-free expression of a desired protein was significantly higher even when a significantly lower concentration of double-stranded concatemeric DNA was employed for the reaction in comparison with that of a plasmid DNA. In some embodiments, the final concentration of the double-stranded concatemeric DNA in the eukaryotic cell-free expression system is in a range from about 0.5 ng/μL to about 20 ng/μL. In certain embodiments, the final concentration of the double-stranded concatemeric DNA in the eukaryotic cell-free expression system is in a range from about 5 ng/μL to about 20 ng/μL. In some other embodiments, the final concentration of the double-stranded concatemeric DNA in the eukaryotic cell-free expression system is in a range from about 2 ng/μL to about 10 ng/μL. In some embodiments, final concentration of the double-stranded concatemeric DNA in the eukaryotic cell-free expression system is in a range from about 3 ng/μL to about 7 ng/μL. In an exemplary embodiment, the final concentration of the double-stranded concatemeric DNA in the eukaryotic cell-free expression system is about 5 ng/μL.

It was observed that cell-free protein expression in eukaryotic lysate was unexpectedly improved by using lower concentration of double-stranded concatemeric DNA (e.g., 0.125 μg of a RCA product DNA in a 25 μL IVTT reaction) compared to using the higher concentrations (e.g., greater than 1 μg of RCA product DNA in a 25 μL IVTT reaction) as a template. For example, applying higher concentrations of RCA DNA template, comprising a TurboGFP gene, than suggested by an IVT kit (e.g., 2 μg, or 3 μg) resulted in lower yields of TurboGFP protein in a cell-free protein expression system, as shown in FIG. 1. However, when the RCA product DNA was used at concentrations that are lower than the suggested concentration per IVT kit protocols (e.g., 500 ng, 250 ng, and 125 ng), elevated expression of the cell-free TurboGFP protein was observed (FIG. 1). The results were comparable using phosphorothioated and non-phosphorothioated RCA product DNA, with marginally better protein expression from the phosphorothioated RCA product DNA. In contrast with the result obtained from RCA product DNA, the protein yield decreased proportionally to the concentration of plasmid DNA template under the same IVTT experimental conditions. For example, 500 ng of plasmid DNA (2× dilution per manufacturer's IVT protocol) yielded less TurboGFP protein compared to that of using 1 μg of plasmid DNA as a template (FIG. 1). Thus, significant improvement of cell-free protein expression was obtained at lower concentration of a RCA product DNA template compared to that of a plasmid DNA template in an IVTT reaction, which was not expected. The increasing trend of the cell-free protein expression (FIG. 1) with decreasing the concentration of RCA product DNA template was also unexpected as compared to general trends of IVTT reaction kinetics, where the cell-free protein expression is directly proportional to the concentration of the template DNA in a typical IVTT reaction.

Generally, higher amount of DNA template is required with increasing reaction volume of IVTT. For example, the 1-step Human High-Yield Maxi IVT kit is formulated for reaction volumes of 2 mL. Per kit protocols, a final concentration of 40 ng/μl plasmid DNA template (i.e., 80 μg of plasmid DNA per 2 mL reaction volume) is required for efficient protein expression in an IVTT experiment. To further scale-up such reaction volume, higher total amounts of plasmid DNA are required, which further increase cost, preparation time and labor. For example, a 4 mL reaction volume would require a total of 160 μg of plasmid DNA to meet a final concentration of 40 ng/μL template. Furthermore, in case of reaction scale-out, the number of IVTT reactions would increase in parallel. As RCA DNA is effective at ~5 ng/μL for cell-free protein expression, approximately 20 μg of total RCA DNA was required to enable 80×25 μL individual reactions instead of 80 μg of total plasmid DNA. As such, the requirement of less amount of RCA product DNA as a template for a cell-free protein expression is advantageous for reaction volume scale-up, reaction volume scale-out, and template cost-control.

To enhance the protein yield from in vitro transcription and translation reactions in mammalian cell-free extract, the removal of waste products is often required as it adversely affects the translation machinery. This is conventionally done using dialysis membranes. Further, the IVTT reaction volume is scaled-up to maximize the concentration of components within the dialysis system. Accordingly, template DNA is also significantly scaled-up to maintain the required concentration of the template DNA in the scaled-up IVTT reaction volume. However, the DNA template is traditionally lost to the solution-based IVTT reaction. To address such concerns and enhance IVTT protein yields, the DNA template may be immobilized onto a substrate to recover the DNA template from the solution-based IVTT reaction. In some embodiments, the immobilized DNA template is exposed to the cell-free expression system under continuous flow such that the protein is produced in a continuous manner from the immobilized DNA template.

In one or more embodiments, the method further comprises immobilizing the double-stranded concatemeric DNA onto a substrate. The substrate used for immobilizing the double-stranded concatemeric DNA template may be selected from a magnetic particle, a sepharose bead, a glass substrate, a polymer substrate or a metal substrate. The magnetic particle may be a magnetic bead or magnetic impeller. The substrate may be or part of a glass test-tube, a petri plate, a multi-well plate, a microfluidic device/system, an analytical device/system, wherein the double-stranded concatemeric DNA can be immobilized on the substrate.

The double-stranded concatemeric DNA may be immobilized onto the substrate by a variety of methods. For example, in one embodiment, the double-stranded concatemeric DNA comprises a biotinylated nucleotide. In such embodiments, the double-stranded concatemeric DNA may be immobilized onto streptavidin-coated substrate through biotin-streptavidin interaction. The step of immobilizing the double-stranded concatemeric DNA onto the streptavidin-coated substrate is performed prior to contacting the double-stranded concatemeric DNA with the eukaryotic cell-free expression system. After immobilizing the double-stranded concatemeric DNA onto the substrate, the eukaryotic cell-free protein expression system is added to the immobilized double-stranded concatemeric DNA, which functions as a template for the in vitro cell-free protein expression. Example 4 clearly demonstrates the cell-free expression from a RCA product DNA generated from DNA mini-circles (see, FIG. 2) and further immobilized on streptavidin beads, wherein the RCA product DNA was biotinylated. The RCA product is immobilized onto streptavidin beads in this example.

In some embodiments, the method further comprises recovering the immobilized double-stranded concatemeric DNA from the reaction mixture comprising the eukaryotic expression system after expressing the protein in vitro. In such embodiments, after expressing the protein, the mixture containing the expressed desired protein and the remaining eukaryotic cell-free expression system may be transferred to a different container. The immobilized double-stranded concatemeric DNA may be washed (e.g., using a washing buffer) before its subsequent use in a subsequent IVTT reaction.

In one or more embodiments, the recovered immobilized double-stranded concatemeric DNA may be re-used in one or more subsequent cell-free expression systems. The recovered immobilized double-stranded concatemeric DNA may be re-used with or without one or more wash steps to remove any impurities carried over from the previous cell-free expression system.

In some embodiments, each of the plurality of tandem repeat sequences of the double-stranded concatemeric DNA comprises an expression sequence comprising a promoter, a CITE, and an ORF, wherein the CITE comprises an internal ribosome entry site (IRES), a translation enhancing element (TEE), or a combination thereof. In some embodiments, the RCA product DNA employed as the double-stranded concatemeric DNA template comprises an IRES sequence as CITE. Numerous examples of suitable IRES or TEE sequences known in the art may be employed as CITE, including those derived from viruses or native sequences within living organisms. The presence of IRES sequence drives efficient translation in eukaryotic cell-free expression system even when the concentration of the RCA product DNA is significantly lower compared to that of a plasmid DNA (as shown in FIG. 1). The RNA folding of IRES elements may affect the regulation of the translational efficiency. In some embodiments, for efficient translation, the components of the cell-free protein expression system such as HeLa cell lysate are optimized such that it ensures effective RNA folding of the IRES elements.

The expression sequence comprises one or more ORFs, wherein each of the ORF includes translational start sequences and translational termination sequences. In certain embodiments, an ORF comprises a codon-optimized sequence, a purification tag sequence, an amino-terminal peptide fusion sequence derived from an IRES for enhanced ribosome recognition, a protease cleavage site, a signal peptide, or combinations thereof. The purification tag sequence may be employed for purification of the expressed protein. In one or more embodiments, the ORF of the expression sequence in each of the plurality of tandem repeat sequences of the double-stranded concatemeric DNA comprises a codon-optimized sequence for enhancing translation. To generate a codon optimized sequence, codon bias, contextual codon preference, and/or individual codon preference are some of the factors that are generally considered.

The codon-optimized sequence of the ORF enhances the rate or quality of translation of the expression sequence in the RCA product DNA. Codon optimization generally improves the protein expression by increasing the mRNA stability or translational efficiency of a gene of interest. The functionality of a gene may also be increased by optimizing codon usage within the custom designed gene. In some codon optimization embodiments, a codon of low frequency in a species may be replaced by a codon with high frequency. For example, a codon UUA of low frequency may be replaced by a codon CUG of high frequency for leucine. In further codon optimization embodiments, a codon representing tRNAs that are highly charged during amino acid starvation may be used. Codon optimization may increase mRNA stability and therefore modify the rate of protein translation or protein folding. Further, codon optimization may customize transcriptional and translational control, modify ribosome binding sites, or stabilize mRNA degradation sites.

In some embodiments, the ORF may include a tag sequence for purification of the expressed protein. The tag sequence may be an affinity tag, a recognition sequence for protease cleavage or combinations thereof. The affinity tag may be used for rapid purification and detection of recombinant proteins. The affinity tag may include a polyhistidine tag (his6) (SEQ ID NO: 8), Glutathione S-transferase tag (GST), haemagglutinin (HA), myc (derived from c-myc gene product), FLAG (consisting of eight amino acids Asp-Tyr-Lys-Asp-Asp-Asp-Asp-Lys (SEQ ID NO: 9) including an enterokinase-cleavage site) or combinations thereof. Although fusion tags help in rapid purification or detection of the desired protein, the tags may not be considered as permanent fixtures or domains of the recombinant proteins. Hence, removal of the fusion tag is often needed for highly analytical studies of recombinant protein structure and function. The tag for purification may be removed from the protein by using another type of tag, such as protease cleavage tag. The protease cleavage tag may be used to cleave a distinct peptide bond within a specific protein or peptide sequence. The protease cleavage tag may include, for example, PreScission Protease tag (GE Healthcare) or thrombin protease tag (GE Healthcare).

In one or more embodiments, each of the plurality of tandem repeat sequences further includes a polyA sequence, an intron sequence, a transcriptional termination sequence, an insulator sequence, or combinations thereof. In some embodiments, each of the tandem repeat sequences further includes a transcription termination sequence and a polyadenylation site, wherein the transcription termination sequence and polyadenylation sites is generally situated at the 3' end of a gene in a DNA template. Transcription termination sequences provide signals in the newly synthesized mRNA to initiate the process of releasing the mRNA from the transcriptional complex, which can also aid in effective translation of the desired protein product.

The effects of inefficient transcription termination in an RCA product derived from a mini-circle are largely inconsequential compared to an RCA product derived from a plasmid DNA. In some cases, plasmid DNA containing a gene of interest must be digested using a restriction enzyme to create a double-stranded DNA break immediately after the gene to prevent transcription from proceeding beyond that point when RCA product is derived from the plasmid. If run-off transcription were to occur, the other sections of the plasmid containing many coding and non-coding sequences (including sequences for the origin of replication, antibiotic selection, and accessory sequences that are used for selection, screening and/or propagation of the plasmid in a host cell) would be transcribed. RCA product derived from the plasmid DNA, when used in an undigested state, may produce unwanted mRNA species, via transcriptional readthrough, that risk production of protein contaminants together with (or in a greater amount than) the protein of interest. However, poor transcription termination in an RCA product derived from a mini-circle may still generate on-target mRNA. Consequently, the yield of cell-free protein is better from an RCA product derived from a DNA mini-circle compared to either an RCA product derived from a plasmid or PCR-amplified plasmid DNA. Similar expression benefits are observed even when the RCA product derived from a DNA mini-circle is completely devoid of transcription termination sequences, which is an unexpected result. These RCA products improve cell-free protein expression by generating tandem repeats of cistronic mRNA species, wherein every cistron of the mRNA comprises the desired target gene. The tandem repeats of the cistron may in turn improve the mRNA stability, particularly when transcription termination signals are absent, and contribute to higher translational flux of the desired protein product.

In one or more embodiments of methods for in vitro transcription and translation, the method includes the steps of providing a circular DNA, generating a double-stranded concatemeric DNA via RCA of the DNA circle, and contacting the generated double-stranded concatemeric DNA with a eukaryotic cell-free expression system in vitro to express a protein from the double-stranded concatemeric DNA via transcription and translation. The final concentration of the double-stranded concatemeric DNA in the eukaryotic cell-free expression system is in a range from about 0.1 ng/μL to 35 ng/μL. In some embodiments, the double-stranded concatemeric DNA is purified prior to contacting with a eukaryotic cell-free expression system. The DNA minicircle may be generated by an intramolecular ligation of a double-stranded DNA template. In one or more embodiments, the double-stranded RCA product DNA, generated from a DNA mini-circle, may be a linear or a branched concatemer.

Figure 3:
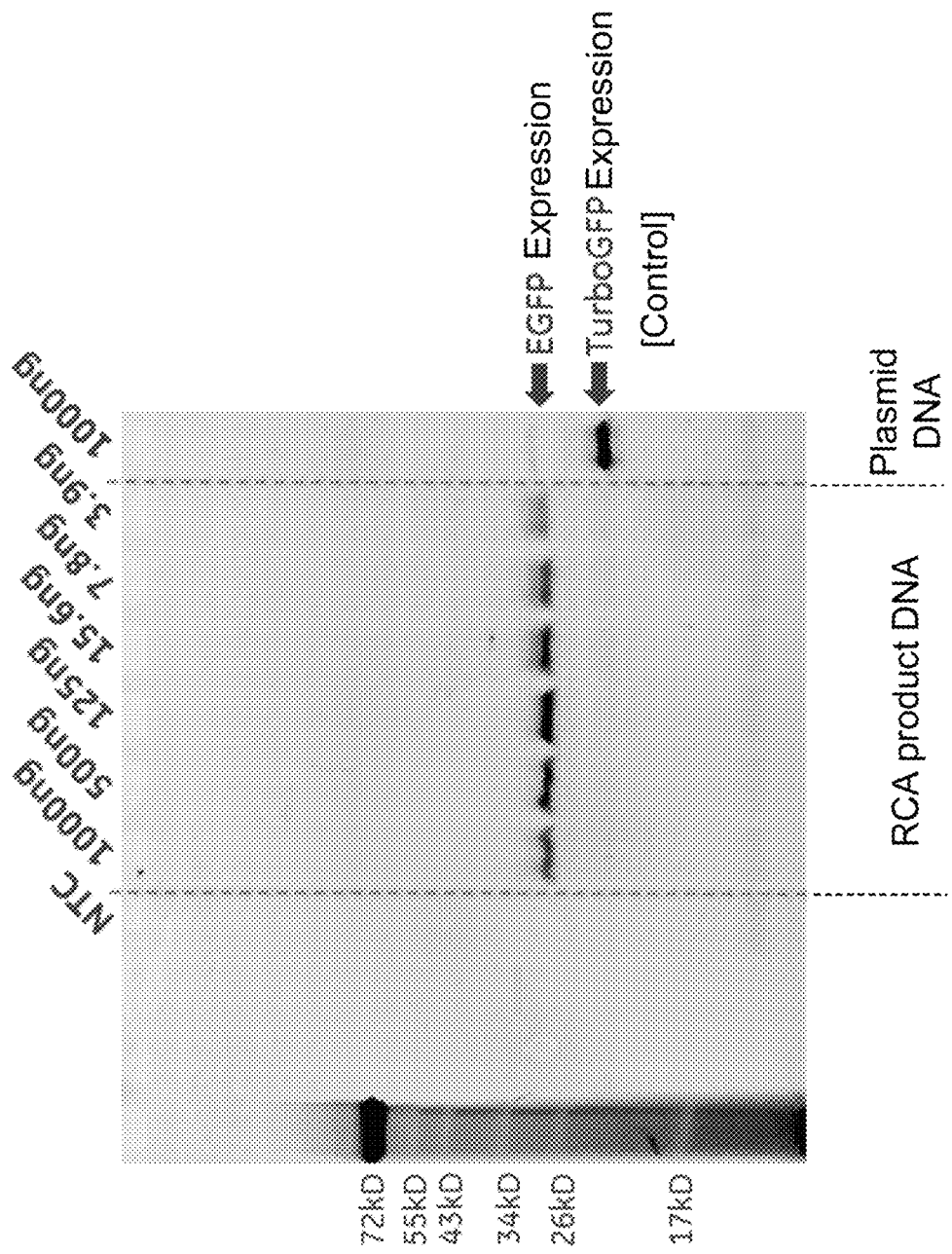
FIG. 3 is an image of an SDS PAGE illustrating cell-free expressions of an enhanced green fluorescent Protein (EGFP), when different concentrations of RCA product DNA derived from a DNA mini-circle were used for in vitro transcription and translation reactions. TurboGFP expression by IVTT of a pCFE-GFP plasmid was used as a control.

In some embodiments, the final concentration of the double-stranded concatemeric RCA product DNA generated from the circular DNA is in a range from about 0.5 to 20 ng/µL. In some other embodiments, the final concentration of the double-stranded concatemeric RCA product DNA generated from a circular DNA in the eukaryotic cell-free expression system is in a range from about 3 ng/µL to about 7 ng/µL. In certain embodiments, the final concentration of the double-stranded concatemeric RCA product DNA generated from circular DNA in the eukaryotic cell-free expression system is in a range from about 5 ng/µL to about 7 ng/µL. In an exemplary embodiment, the final concentration of the double-stranded concatemeric RCA product DNA generated from DNA circles in the eukaryotic cell-free expression system is about 5 ng/µL. Example 3, FIGS. 2 and 3 show that the requirement of RCA product DNA generated from a DNA circle is 4 to 8-fold lower than the plasmid DNA for desired protein expression in the eukaryotic cell-free lysate.

The double-stranded RCA product DNA used for IVTT reaction, generated from a DNA mini-circle, may be a linear or a branched concatemer. The DNA mini-circle consists essentially of a minimalistic expression sequence consisting essentially of a promoter, a cap-independent translation element, and an ORF. Thus, the linear or branched concatemer (double-stranded RCA product DNA) generated from the DNA mini-circle consists essentially of tandem repeats of a minimalistic expression sequence. The ORF of minimalistic expression sequence is a nucleic acid sequence containing a particular gene of interest. The minimalistic expression sequence may also contain minimal genetic elements or sequences that are needed for expression (for example, an enhancer sequence) of the gene of particular interest.

In one or more embodiments, the ORF of the minimalistic expression sequence comprises a codon-optimized sequence, a purification tag sequence, a protease cleavage site or combinations thereof. To generate a codon optimized sequence, codon bias, contextual codon preference, and/or individual codon preference are the factors which are generally considered. As noted, in some embodiments, the minimalistic expression sequence further consists essentially of a transcription termination sequence.

The cap-independent translation element (CITE) of the DNA mini-circle comprises an internal ribosome entry site (IRES), a translation enhancing element (TEE), or a combination thereof. The minimalistic expression sequence may further contain an insulator sequence, a polyA sequence, a transcriptional termination sequence, or a combination thereof. It may additionally contain sequences that do not materially affect the in vitro transcription and/or translation of the double-stranded concatemeric RCA product DNA. For example, it may further include sequences such as a translational enhancer sequence, an insulator sequence, an intron sequence, or a transcriptional termination sequence. However, the minimalistic expression sequence and the resulting double stranded RCA product do not include any additional sequences that may negatively impact the in vitro transcription and translation of the RCA product.

Numerous examples of suitable promoters known in the art may be employed, including, for example, T7 RNA polymerase promoter sequences. Likewise, numerous examples of suitable ribosomal binding sites are known in the art, including for examples internal ribosome entry sites (IRES), polyA tracts, species-independent translational leaders (SITS), Kozak consensus sequences, and Shine-Dalgarno sequences. The insulator sequence generally enhances the efficiency of ribosomal binding or translational initiation. Numerous examples of suitable insulator sequences exist in the art, including for example, sequences encoding the translated N-terminus of native IRES ORFs, or poly-histidine tracts. The minimalistic expression sequence may further include a pre-promoter sequence, a sequence for protease cleavage or nucleotide cleavage, a sequence for protein purification, or combinations thereof. The minimalistic expression sequence is selected such that it does not contain any sequences that hampers or inhibits either the transcription and/or translation of the desired protein product or otherwise make the protein production more cumbersome.

The minimalistic expression sequence is devoid of any extraneous sequences that are required for propagation of a plasmid in a host cell. For example, the RCA product excludes any extraneous sequences, such as an origin of replication, antibiotic selection gene, or any other accessory sequences that are required for cloning, selection, screening and/or replication in a host cell. The presence of such extraneous sequences in the RCA product would materially affect the transcription and/or translation in a cell-free protein expression. The "extraneous sequences" includes the sequences which are not necessary for coding or expression of a desired protein. The extraneous sequences may include the accessory sequences that are used for selection, screening, and/or propagation of a plasmid in a host cell, such as lacZ, beta-galactosidase. The extraneous sequences may include sequences for origin of replication, antibiotic selection gene, suitable restriction sites for insertion of a gene, such as multiple cloning sites, or combinations thereof. The extraneous sequence may further comprise any other sequence required for cloning into a host cell or detection in a host cell.

The double-stranded concatemeric RCA product DNA sequence may comprise a phosphorothioated nucleotide, a biotinylated nucleotide, or a combination thereof. In certain embodiments, the double-stranded concatemeric RCA product DNA consisting essentially of tandem repeats of a minimalistic expression sequence comprises a biotinylated nucleotide. In such embodiments, the method further includes immobilizing the double-stranded concatemeric DNA including a biotinylated nucleotide onto a substrate prior to containing the double-stranded concatemeric DNA with the eukaryotic cell-free expression system, wherein the substrate is a streptavidin-coated substrate. The method further includes recovering the immobilized double-stranded concatemeric DNA from the eukaryotic cell-free expression system after expressing the protein in vitro from the double stranded concatemeric DNA. The method further includes re-using the recovered double-stranded concatemeric DNA template consisting essentially of tandem repeats of a minimalistic expression sequence for subsequent IVTT reactions.

The RNA polymerases used in cell-free transcription reactions (for example, T7 RNA polymerase) generally require double-stranded DNA promoter sequences for effective binding to DNA coding sequences. The effective binding of RNA polymerase to the double-stranded DNA promoter sequence initiates efficient transcription. Thus, RCA reaction conditions that promote the generation of double-stranded RCA products are desired for effective in vitro transcription and translation.

In some embodiments, the generated double-stranded concatemeric DNA needs to be cleaned up before contacting with the eukaryotic cell-free expression system. In some embodiments, the RCA product DNA may be separated (e.g., by precipitation) to remove salts or any other contaminants, such as primers or smaller fragmented DNA from the reaction medium before proceeding for cell-free expression using a eukaryotic cell-extract. In some embodiments, the double-stranded RCA product DNA is provided to the cell-free expression system without any further processing. For example, the RCA product DNA may be added to the cell-free system directly after amplification without any further restriction digestion.

The minimalistic expression sequence includes a promoter sequence, present upstream (5') of the gene of interest to be transcribed. DNA-dependent RNA polymerases bind to the double-stranded DNA promoter region to initiate gene transcription. A variety of suitable RNA polymerases is known in the art and includes those having only one subunit (for example, those from bacteriophages like T3 and T7, and mitochondria) as well as multi-domain RNA polymerases derived from bacteria and eukaryotes. The RNA polymerase may further require additional protein co-factors for efficient transcription.

In some embodiments of the cell-free transcription-translation reaction, a biomolecular transcriptional/translational machinery is extracted from cells and utilized for in vitro translation. The composition, proportion of enzymes, and building blocks required for transcription and translation are provided by this cell-free extract. The mRNAs synthesized by transcription are expressed in a translation reaction, which produces the target protein in the cell-free extract. In the in vitro expression reaction, protein synthesis occurs in cell-free extract rather than within cultured cells (the extracted material from cells may be referred to herein as a "cell-free extract" or "cell extract" which does not contain any intact cells). The cellular extract contains generally the cytosolic and organelle components of the cell. The cell-free extract may supply all or most of the molecules required for cell-free transcription and translation, such as ribosomes, translation factors, tRNA and amino acids, enzymatic cofactors and an energy source, and cellular components essential for protein folding. In the in vitro protein expression reaction, protein synthesis occurs in cell-free extract rather than within cultured intact cells.

As noted, in some embodiments, the cell-free expression system comprises a eukaryotic cell extract, wherein the cell extract is derived from unicellular organism (e.g., protozoans, yeast cells, insect cells) or multi-cellular organism (e.g. insect cells, mammalian cells including human cells). Suitable eukaryotic cell extract includes, but not limited to, rabbit reticulocyte lysates (RRL), wheat germ extracts, insect cell lysates (such as SF9 or SF21), mammalian lysates (such as CHO), human lysates (such as HeLa), or protozoan lysate (such as *Leishmania*).

The mRNA derived from RCA product DNA may be added to, or produced within, the eukaryotic cell extract. The DNA template used for RCA reaction may be a synthetic DNA or a natural DNA. The DNA template may be a circular DNA template. In one example embodiment, the circularization of a linear nucleic acid template is accomplished by an enzymatic reaction, for example, by incubation with a ligation enzyme such as DNA ligase. In some embodiments, the DNA mini-circle template includes a minimalistic expression sequence. The RCA product used for in vitro transcription-translation may be an intact, non-degraded state.

The rolling-circle amplification reaction often employs reagents such as a primer, a polymerase, and free nucleotides (dNTPs). In some embodiments, RCA may be performed by contacting a double-stranded DNA mini-circle with a primer solution comprising a random primer mixture to form a nucleic acid template-primer complex; contacting the nucleic acid template-primer complex with a DNA polymerase and deoxyribonucleoside triphosphates; and amplifying the nucleic acid template. The nucleic acid polymerase that is employed in the amplification reaction may be a proofreading nucleic acid polymerase. RCA may be performed by using any of the DNA strand-displacing polymerases that are known in the art, including, but not limited to, a Phi29 DNA polymerase. The amplification reaction mixture may further include additional reagents such as suitable amplification reaction buffers.

In some embodiments, each of the reagents used in the nucleic acid amplification reaction may be pre-treated to remove any contaminating nucleic acids. In some embodiments, the pre-treatment of the reagents includes incubating the reagents in presence of ultraviolet radiation. In some other embodiments, the reagents are de-contaminated by incubating the reagents in presence of a nuclease and its co-factor (for example, a metal ion). Suitable nucleases include, but are not limited to, exonucleases such as exonuclease I or exonuclease III. In some embodiments, the proofreading DNA polymerases used for DNA amplification reaction may be de-contaminated by incubating with a divalent metal ion (for example, magnesium or manganese ions) in absence of dNTPs.

The RCA reaction may be performed using a random primer mixture. In some embodiments, specific primers are used for the RCA reaction. Primer sequences comprising one or more nucleotide analogues may also be used. In one or more embodiments, the RCA is performed using a random primer mixture comprising a nucleotide analogue. In some embodiments, the RCA is performed using dNTPs containing a nucleotide analogue. The nucleotide analogue may be an inosine, a Locked Nucleic Acid (LNA) nucleotide, a Peptide Nucleic Acid (PNA) nucleotide, a thioated nucleotide, 2-amino-deoxyadenosine, 2-thio-deoxythymidine, a polycation nucleotide, Zip Nucleic Acid (ZNA), polycation modified nucleotide, or combinations thereof. In one or more embodiments, the random primer mixture has a sequence +N+N(atN)(atN)(atN)*N (SEQ ID NO: 6) (AT hexamer Primer). In some embodiments, nuclease-resistant primers (e.g., primer sequences comprising phosphorothioate groups at appropriate positions) are employed for the amplification reactions (e.g., NNNN*N*N). In some embodiments, the amplification of the DNA mini-circles employs random hexamers or a hexamer primer, +N+N(at N)(at N)(at N)*N (SEQ ID NO: 6) (AT hexamer primer).

During the amplification reaction, the DNA template, for example, a DNA mini-circle consists essentially of a minimalistic expression sequence, is replicated by a polymerase in the presence of deoxyribonucleoside triphosphates (dNTPs) or their modified counterparts. The free nucleotides employed in nucleic acid template amplification may include natural nucleotides (for example, dATP, dGTP, dCTP or dTTP) or their modified analogues. In some embodiments, the reaction mixture is supplemented with thioated dNTPs. The thioated dNTPs may include but are not limited to α-S-dGTP, α-S-dCTP, α-S-dATP, and α-S-dTTP. The thioated dNTPs such as α-S-dATP or α-S-dTTP may be added into the dNTP mixture for random incorporation of the thioated bases into the RCA product.

In some embodiments, the RCA is performed using a final concentration of dNTPs in a range of about 10 μM to about 10 mM. In one or more embodiments of RCA reactions, the dNTP concentration is less than 10 mM. In these embodiments, the concentration of dNTPs is kept lower than 10 mM to avoid hydrogel formation from the RCA product and to remain at a concentration below or equal to the amount of divalent cation (e.g., Mg2+) present in the reaction buffer. Hydrogel formation may occur after amplification in the presence of a high concentration of dNTPs which may further complicate the downstream manipulation such as pipetting and processing of the RCA product. Hydrogel formation may be observed when dNTP concentration of 50 mM or more is used in the RCA reaction.

RCA may be performed using commercially available RCA amplification kits such as Illustra™ TempliPhi™ Amplification Kit (GE Healthcare). TempliPhi rolling-circle amplification employs modified random primers, which provide higher sensitivity and amplification balance. In some embodiments, nuclease-resistant primers are used for RCA reaction. Since high concentration of template DNA is required for the present method of in vitro transcription and translation, a more balanced DNA amplification with faster kinetics and higher yield may be achieved using RCA.

A variety of methods may be used to prepare a DNA mini-circle template for use with methods of the invention. In some embodiments, a linear DNA template may be circularized to generate a DNA mini-circle template. In one example embodiment, the circularization of the linear DNA template may be effected by an enzymatic reaction, for example, by incubation with a ligation enzyme such as DNA ligase. In some embodiments, the terminal ends of the linear DNA template are hybridized to a nucleic acid sequence such that the terminal ends come in close proximity. Incubating with a ligation enzyme may then effect the circularization of the hybridized linear DNA template to generate a DNA mini-circle. Suitable DNA mini-circle template may also be generated by PCR amplification of a portion of a larger DNA (for example, a genomic DNA, or a DNA from a DNA library) using appropriate PCR primers, followed by circularization of the PCR product. DNA mini-circle may also be generated by chemical synthesis of suitable linear oligonucleotides followed by circularization of the synthesized oligonucleotide. In some embodiments, the synthesized linear oligonucleotides may consist essentially of minimalistic expression sequence and achieve circularization via DNA ligase to generate DNA mini-circle.

One or more of the methods may further comprise steps of purifying, analyzing and/or quantifying the DNA mini-circles. Isolation or purification of the double-stranded DNA mini-circles and/or removal of the contaminants, such as enzymes or non-ligated form of DNA may be performed prior to the amplification reaction. Any suitable techniques that are used for purification, analysis or quantification of nucleic acids may be employed. Non-limiting examples include precipitation, filtration, affinity capture, gel electrophoresis, sequencing or HPLC analysis. For example, the purification of the circular nucleic acids may be achieved by affinity capture. In some embodiments, the methods may further comprise processing of the generated DNA mini-circle. Post-processing of the generated DNA mini-circle may vary according to the intended use.

EXAMPLES

Unless specified otherwise, ingredients described in the examples are commercially available from common chemical suppliers. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

Materials: 1-Step Coupled IVT kits using human and CHO lysates, pCFE-GFP control vector, and Quant-IT PicoGreen® double-stranded DNA Assay kit were purchased from ThermoFisher, Waltham, Mass., USA. MICROCON® centrifugal filters and Streptavidin magnetic beads were purchased from Sigma-Aldrich, St. Louis, Mich., USA. PstI enzyme was purchased from New England Biolabs, Ipswich, Mass., USA. Typhoon variable-mode Imager was obtained from GE Healthcare, Piscataway, N.J., USA. SpectraMax M5 Microplate Reader was from Molecular Devices, LLC.

Example 1: Generation of a RCA Product DNA

The RCA product DNA was generated either from a circular DNA template (either a plasmid positive control e.g., pCFE-GFP, or from a DNA mini-circle having minimalistic expression sequence) by an RCA reaction. The plasmid positive control, pCFE-GFP, was purchased as part of the 1-Step Human Coupled IVT kit. This purified plasmid comprises an internal ribosomal entry sites (IRES) of encephelomyocarditis virus (EMCV) and encodes TurboGFP protein.

Generation of a DNA Mini-Circle:

Minimalistic expression sequences for EGFP were designed in silico and synthesized in vitro. The minimalistic expression sequences primarily contained a T7 promoter and +1 sequence (first ribose position of the 5'-untranslated region of the resulting mRNA) followed by an IRES sequence fused to the EGFP coding region. A variety of additional non-coding and coding parameters were included during the designing of the minimalistic expression sequence, including T7 pre-promoter sequences, T7 phi10 promoter stem loops, translation enhancing elements (TEE), ribosomal binding sequences, insulator sequences for enhancing ribosomal binding, insulator sequences for enhancing ribosomal initiation, T7 transcription termination sequences, polyadenylation sequences, peptide leader-sequences, or protease cleavage sites. The minimalistic expression sequence may further be optimized for codon usage. A representative minimalistic expression sequence is listed as SEQ ID No. 5 (Table 3). The minimalistic expression sequence of SEQ ID No. 5 comprises sequentially, T7 promoter, EMCV IRES, translational start codon, translated N-terminus of EMCV polyprotein ORF (fused to EGFP, which is codon optimized), translational stop codons, polyA tract and T7 transcriptional terminator sequence.

TABLE 3

DNA sequence list

| SEQ ID No. | Sequences |
|---|---|
| 5 | CCGGGATCCCAGTGAATTGTAATACGACTCACTATAGGGC GAATTAATTCCGGTTATTTTCCACCATATTGCCGTCTTTTGG CAATGTGAGGGCCCGGAAACCTGGCCCTGTCTTCTTGACGA GCATTCCTAGGGGTCTTTCCCCTCTCGCCAAAGGAATGCAA GGTCTGTTGAATGTCGTGAAGGAAGCAGTTCCTCTGGAAG CTTCTTGAAGACAAACAACGTCTGTAGCGACCCTTTGCAGG CAGCGGAACCCCCCACCTGGCGACAGGTGCCTCTGCGGCC AAAAGCCACGTGTATAAGATACACCTGCAAAGGCGGCACA ACCCCAGTGCCACGTTGTGAGTTGGATAGTTGTGGAAAGA GTCAAATGGCTCACCTCAAGCGTATTCAACAAGGGGCTGA |

TABLE 3-continued

DNA sequence list

| SEQ ID No. | Sequences |
|---|---|
| | AGGATGCCCAGAAGGTACCCCATTGTATGGGATCTGATCT<br>GGGGCCTCGGTGCACATGCTTTACATGTGTTTAGTCGAGGT<br>TAAAAAACGTCTAGGCCCCCCGAACCACGGGGACGTGGTT<br>TTCCTTTGAAAAACACGATGATAATATGGCCACAACCGTG<br>AGCAAGGGCGAGGAGCTGTTCACCGGGGTGGTGCCCATCC<br>TGGTCGAGCTGGACGGCGACGTAAACGGCCACAAGTTCAG<br>CGTGTCCGGCGAGGGTGAAGGCGACGCTACTTACGGAAAG<br>CTGACACTGAAGTTCATTTGCACCACAGGCAAACTGCCTGT<br>GCCCTGGCCAACCCTCGTGACTACCCTCACATACGGCGTGC<br>AGTGCTTTAGCAGATATCCTGATCATATGAAACAGCACGA<br>CTTCTTTAAGTCTGCTATGCCTGAAGGATACGTGCAGGAGA<br>GAACCATCTTCTTCAAGGACGACGGAAACTATAAGACTAG<br>AGCCGAGGTGAAGTTTGAGGGAGACACACTGGTGAATAGG<br>ATCGAGCTGAAGGGCATTGACTTCAAGGAGGACGGAAACA<br>TCCTGGGCCACAAGCTGGAGTACAACTACAATAGCCACAA<br>CGTCTATATTATGGCTGATAAGCAGAAGAACGGAATCAAG<br>GTGAACTTCAAGATCAGACACAACATCGAGGACGGCAGCG<br>TGCAGCTGGCCGACCACTACCAGCAGAATACCCCTATCGG<br>AGACGGCCCCGTGCTCCTGCCAGACAACCACTACCTGAGC<br>ACCCAGTCCGCCCTGAGCAAAGACCCCAACGAGAAGCGCG<br>ATCATATGGTTCTGCTGGAGTTCGTGACCGCCGCCGGCATC<br>ACTCTTGGTATGGACGAGCTGTACAAGTAATAAGATCTGA<br>CTGAAAAAAAAAAAGTTTAAACACTAGTCCGCTGAGCAAT<br>AACTAGCATAACCCCTTGGGGCCTCTAAACGGGTCTTGAG<br>GGGTTTTTTGCTGCAGAGATCTCCG |
| 6 | +N+N(at N)(at N)(at N)*N |
| 7 | biotin-NNNN*N*N |

Linear double-stranded DNA was synthesized using a DNA synthesizer (Integrated DNA Technologies, Inc.) with unique restriction sites at both the 5' and 3' ends (BamHI and BglII, respectively). To create the DNA mini-circle, the double-stranded DNA was digested with both endonucleases to produce complementary sticky overhangs. This digested DNA was ligated using T4 DNA ligase. Restriction digestion and ligation steps were carried out either sequentially or simultaneously (e.g., in the same tube) using reaction mixtures comprising 20 U BamH1, 10 U BglII, 400 U T4 ligase, 1 mM ATP, 100 µg/mL bovine serum albumin (BSA), 100 mM NaCl, 10 mM MgCl$_2$, 50 mM Tris-HCl, pH 7.5, and 10 mM dithiothreitol (DTT). All ligation products (DNA mini-circle) were subsequently treated with Exonuclease I and Exonuclease III to digest any remaining linear DNA fragments. The Exonucleases were heat inactivated by incubating the ligation products at 80° C. for 20 min. After heat-inactivation of the exonuclease, 10 µl (10 ng of circular DNA) of the completed ligation reaction was denatured and then employed directly (with no intermediate purification) for isothermal RCA reactions using Phi29 DNA polymerase.

Rolling-Circle Amplification (RCA):

RCA of a circular DNA template (e.g., a plasmid or a DNA mini-circle) yields a high molecular weight, hyper-branched concatemer having tandem repeats of the input DNA sequence. RCA reagents, including water, reaction buffer, primers, and DNA polymerase enzyme were pre-cleaned at 30° C. for 60 minutes prior to the addition of the circular DNA template (plasmid or mini-circle) or dNTPs to minimize off-target amplification. In some embodiments, primer-nucleotide mix comprising exonuclease-resistant primer and nucleotides was decontaminated by incubating the primer-nucleotide mix with a combination of exonuclease I, exonuclease III, and a single stranded DNA binding protein (SSB protein). In some embodiments, an enzyme mix containing a strand-displacing DNA polymerase was decontaminated by incubating with a divalent cation (e.g., Mg$^{2+}$) optionally in presence of an exonuclease (if the DNA polymerase used included a non-proof-reading DNA polymerase). The amplification of the circular DNA template was subsequently performed using the decontaminated enzyme and primer-nucleotide mixes. For example, a polymerase solution containing 200 ng of Phi29 DNA polymerase was incubated with 0.1 unit of exonuclease III in 5 µL of 50 mM HEPES buffer (pH=8.0) containing 15 mM KCl, 20 mM MgCl$_2$, 0.01% Tween-20 and 1 mM TCEP. The incubation was performed either at 30° C. for about 60 min. or at 4° C. for 12 h. The decontaminated Phi29 DNA polymerase solution was transferred to an ice-bath and then was used in the target RCA assay without prior inactivation of the exonuclease III.

The amplification of the circular DNA (either the plasmid or the DNA mini-circle) was performed using random hexamers, or hexamer primers having the sequence +N+N (at N)(at N)(at N)*N (AT hexamers, SEQ. ID. No. 6), where "N" represents a random nucleotide (i.e., N may be any of A, C, G, or T/U), "at N" represents any of 2-amino dA, 2-thio dT, normal G or normal C, a plus (+) sign preceding a letter designation denotes that the nucleotide designated by the letter is a locked nucleic acid (LNA) nucleotide, and a star (*) sign preceding a letter denotes that the nucleotide designated by the letter is a phosphorothioate modified nucleotide. In some embodiments, the amplification of circular DNA was performed using biotinylated hexamers having the sequence biotin-NNNN*N*N (SEQ. ID. No. 7), where "N" represents a random nucleotide (i.e., N may be any of A, C, G, or T/U), and a star (*) sign preceding a letter denotes that the nucleotide designated by the letter is a phosphorothioate modified nucleotide. For all RCA reactions, the dNTP concentration was maintained below 1 mM (typically 400-800 µM) to avoid hydrogel formation of the amplified RCA product DNA, which can potentially complicate the downstream usability of the RCA product DNA.

DNA amplification reactions were performed by incubating pre-cleaned RCA reagents at 30° C. for about 16 hours or 960 min with the circular DNA template and nucleotide mix. For rolling-circle amplification, the amplification reaction mixture comprised 40 µM primer, 400 µM dNTPs (400 µM each of dATP, dCTP, dGTP, dTTP); ~1-30 ng of circular DNA template (either the plasmid or the DNA mini-circle), 20 ng/µL of phi29 DNA polymerase, 50 mM HEPES (pH=8.0), 30 mM KCl, 20 mM MgCl$_2$, 2.5% (w/v) PEG-8000, 0.01% (v/v) Tween-20, and 1 mM TCEP. At the end of the incubation, the Phi29 DNA polymerase in the reaction mixture was inactivated by heating the reaction mixture at 65° C. for 10 minutes. In some examples, thioated dATP was supplemented at a 1:40 ratio (e.g., 0.01 mM alpha-S-dATP) relative to non-thioated dATP within the dNTP solution.

The RCA product DNA was generated from the DNA mini-circle derived from SEQ ID No. 5. To generate the DNA mini-circle, the DNA template of SEQ ID No. 1 was digested with BamHI and BglII and circularized by ligation. RCA reactions using pCFE-GFP plasmid and the DNA mini-circle were performed under three different test conditions, (i) using random hexamers and dNTPs, (ii) using AT-hexamer primers and dNTPs; and (iii) using AT hexamers and dNTPs mixed with thioated dATPs. All RCA reactions comprised 0.4 mM dNTP (final concentration of dNTP, and optionally thioated dATPs) and 40 µM of primer (either random hexamer, AT hexamer, or biotinylated hexamer), except that phosphorothioated dATP was added at a 1:40 ratio (e.g., 0.01 mM alpha-S-dATP) relative to non-thioated dATP for some reactions. RCA products were quantified using Quant-It™ Picogreen® double-stranded DNA Assay Kit (ThermoFisher Inc.) from a total RCA reaction volume of 100 µL. Agarose gel electrophoresis of the restricted DNA products was also performed, and the intensity of the electrophoresis bands was compared to those of standards having known concentration of DNA.

Example 2: Expression of the RCA Product DNA Generated from a Plasmid DNA in a Eukaryotic Cell-Free Extract 1-Step Human Coupled IVT kit includes a pCFE-GFP as a positive control vector containing the internal ribosomal entry sites (IRES) of encephelomyocarditis virus (EMCV) and encoding a TurboGFP protein. As the RNA folding of IRES sequence is known to significantly affect the regulation of translation efficiency, the components within the 1-Step in vitro transcription translation (IVTT) kit have been optimized for EMCV IRES activity.

The pCFE-GFP control vector was amplified by RCA using AT primers (SEQ. ID. No. 6) in the presence or absence of thioated dATP, as described in Example 1. In vitro transcription-translation assays using 1-Step Coupled IVT were performed per manufacturer instructions. One microgram of RCA product DNA, without any intermediate purification, was added to Hela-cell lysate (250 µL final volume) and was incubated at 30° C. for 6 hours in an Eppendorf ThermoMixer® to perform in vitro transcription and translation (IVTT) of the RCA product DNA. Translated cell-free TurboGFP protein was incubated overnight at 4° C. prior to fluorescence quantitation. A 4-fold diluted sample (in PBS) containing the TurboGFP protein generated by IVTT was subjected to fluorescence measurement using a SpectraMax M5 Microplate Reader. The fluorescence of active cell-free TurboGFP protein was measured at 482 nm and compared to a purified green fluorescence protein (GFP) as a reference (BioVision, Inc). Total cell-free TurboGFP protein yield was calculated in units of µg/mL. FIG. 1 shows that virtually no fluorescent TurboGFP was produced from RCA products when applied directly into Hela lysate without any intermediate clean-up or purification.

Since RCA reaction components might inhibit the IRES-mediated translation of the IVTT to remove the RCA reaction components, RCA product DNA was precipitated by adding 0.04 volume of 500 mM EDTA and 0.1 volume of 7.5 M ammonium acetate and mixed by vortexing. To the mixture, 3.5 volume of 95% ethanol (at room temperature, 25° C.) was added and re-mixed prior to pelleting the RCA product DNA at 20,000 g at room temperature in a microcentrifuge for 20 minutes. The supernatant was carefully removed from the tube using a pipette without touching the DNA pellet. Approximately 200 µL of 70% ethanol (room temperature) was then added to the pellet, subjected to vortexing to mix, and re-centrifuged at 20,000 g for 5 minutes. The supernatant was carefully removed without touching the pellet. After re-spinning the DNA pellet in microcentrifuge at the speed of 20,000 g for 3 minutes, the last traces of ethanol were removed (being careful to avoid over-drying, which might render the RCA DNA insoluble). The DNA pellet was then re-suspended in 0.1 M TE buffer (10 mM Tris, pH7.5, 0.1 mM EDTA) and stored at 4° C. prior to use in cell-free expression reactions.

Cell-free protein expression using purified RCA DNA was subsequently determined using Hela cell lysate. One microgram of purified RCA DNA was added to the Hela cell lysate and IVTT assay was performed using 1-Step Human Coupled IVT kit per manufacturer protocol. FIG. 1 shows that TurboGFP protein yield from RCA product DNA was comparatively less than plasmid DNA when 1 µg of RCA DNA was used for IVTT reaction. Applying RCA product DNA in 2× or 3× higher concentration in IVTT reaction (2 µg and 3 µg) resulted in even lower yields of TurboGFP protein (as shown in FIG. 1). When the RCA DNA was diluted by 2×, 4×, and 8× (500-125 ng) relative to a concentration suggested by the 1-Step Human Coupled IVT kit and used for IVTT, an increased cell-free TurboGFP protein yield was observed, which is presented in FIG. 1. As the total IVTT reaction volume was 25 µL, the final concentration of RCA template DNA was in a range between 5-20 ng/µL. Cell-free expression results were comparable between thioated and non-thioated RCA product DNA. In contrast, when plasmid DNA was used as a template, upon dilution of the plasmid DNA, cell-free protein expression yield was decreased in IVTT. For example, 0.5 µg of plasmid DNA template (2× dilution) yielded less TurboGFP protein compared to the 1 µg of plasmid DNA, as shown in FIG. 1.

Figure 4:
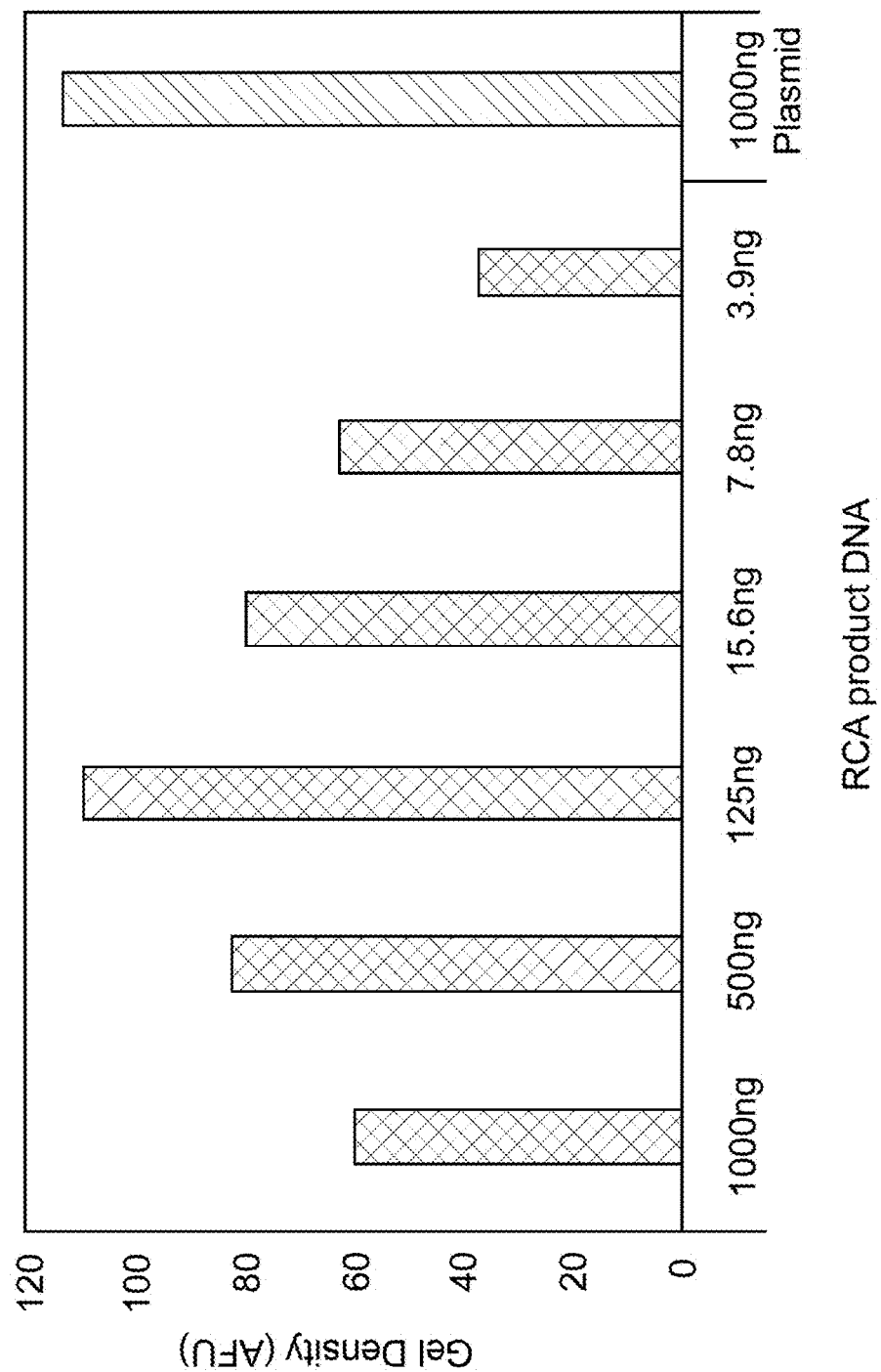
FIG. 4 illustrates comparative cell-free expression of an enhanced green fluorescent protein (EGFP) using different concentrations of a RCA product DNA derived from a DNA mini-circle with that of a plasmid DNA template as control, generated by gel densitometry of the SDS-PAGE of FIG. 3.

Example 3: Cell-Free Protein Expression Using RCA Product DNA Generated from the DNA Mini-Circle Data from Example 2 (FIG. 1) showed that when RCA product DNA was used as a template for IVTT assay using HeLa cell lysate, a 4 to 8-fold lower concentration of the RCA product DNA was required for optimal protein expression in comparison to the plasmid DNA. This observation was further established by using an RCA product DNA generated from a DNA mini-circle for IVTT reactions. The RCA product DNA generated from the DNA mini-circle template was prepared and utilized to compare protein expression by IVTT. A DNA sequence (SEQ ID No. 5) encoding an EGFP protein was ligated to form a mini-circle and amplified by RCA using AT primers in the presence of thioated dATP, as described in Example 1. The RCA product DNA was serially diluted to generate samples of the RCA product DNA with different concentrations. Different concentrations of the RCA product DNA were added to 25 µL of 1-Step Human Coupled IVT reaction mixture and incubated at 30° C. for 6 hours in an Eppendorf ThermoMixer with mild shaking at 300 rpm. The generated IVTT product, a cell-free EGFP protein, was allowed to fold overnight at 4° C. prior to fluorescence analysis. Approximately 4 µL of the IVTT product was separated by SDS-PAGE (FIG. 3) and native fluorescent protein was detected in the gel using a 488 nm Typhoon variable-mode Imager (GE Healthcare). FIG. 4 demonstrates that approximately 125 ng of the RCA product DNA produced maximal cell-free expression of EGFP in HeLa cell lysate, which is consistent with the results of Example 2 using the RCA product DNA generated from the plasmid DNA template. A Gaussian distribution was observed among the RCA product DNA expression yields as shown in FIG. 4. Consequently, FIG. 4 illustrates that nearly equivalent amounts of protein were generated from 0.5-1 micrograms of input RCA DNA and as from 8-16 nanograms of input RCA DNA. FIG. 4 further shows that the cell-free protein expression was almost same even when the difference between the amount of input RCA DNA (such as the input of 0.5 micrograms and 16 nanograms) was greater than 96%. For control purposes, TurboGFP protein was synthesized from 1 microgram of pCFE-GFP plasmid (per kit manufacturer instructions) to compare relative fluorescence output. In summary, FIGS. 3 and 4 show that the requirement of the RCA product DNA generated from circular template (DNA mini-circle construct of FIG. 2) is 4- to 8-fold lower than that of the plasmid DNA for desired protein expression in the eukaryotic cell-free lysate.

Figure 5:
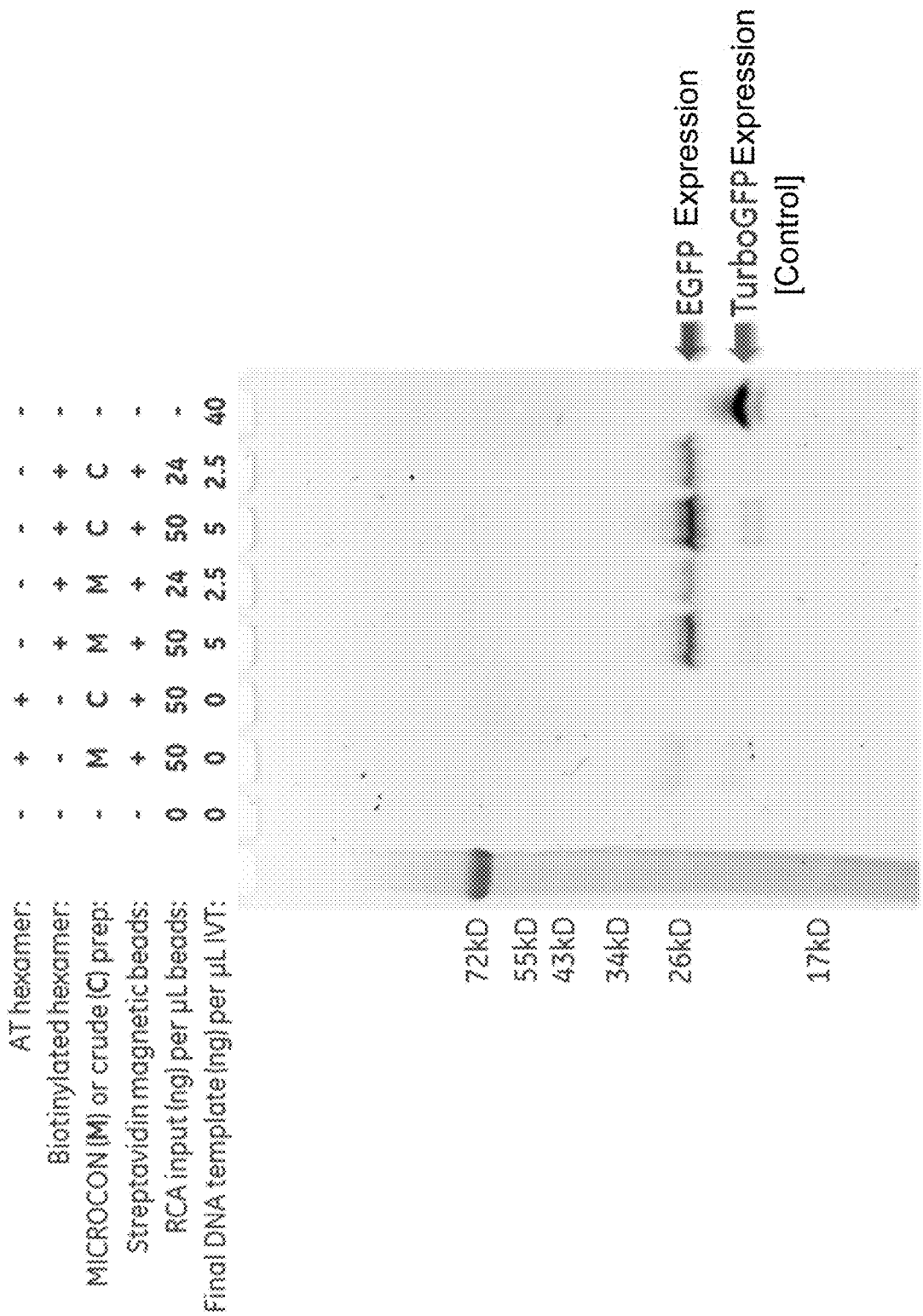
FIG. 5 illustrates cell-free expression of an enhanced green fluorescent protein (EGFP) when an RCA product DNA derived from a DNA mini-circle is conjugated to magnetic beads and used as template for in vitro transcription and translation, with a non-conjugated plasmid DNA template encoding TurboGFP as control.

Example 4: Cell-Free Expression from Magnetic Bead-Conjugated RCA Product DNA Generated from DNA Mini-Circles A biotinylated RCA product DNA generated from the DNA mini-circle sequence (SEQ ID No. 5) from Example 3 was conjugated onto streptavidin beads, and used for in vitro transcription and translation in HeLa cell extract. The DNA mini-circle (SEQ ID No. 5) was amplified by RCA using a biotinylated hexamer primer (SEQ ID. No. 7) or a non-biotinylated AT hexamer (SEQ ID. No. 6) primer, and the resulting amplification products were quantified by PicoGreen assay. In some embodiments, the resulting crude RCA product was pre-purified using MICROCON centrifugal filters to remove excess biotinylated hexamer primers prior to bead conjugation. Either crude or purified RCA product DNA was mixed with streptavidin beads to achieve the potential for approximately 24 ng or 50 ng of the RCA product DNA captured per microliter of beads. The relative amounts of the RCA product DNA conjugated onto the streptavidin beads was confirmed by digesting the streptavidin beads with PstI and quantifying the amount of DNA released by PicoGreen assay. Quantitative results from a representative bead-preparation protocol are presented in Table 3. After extensive washing of the beads in PBS using a magnet to collect, a fixed volume (2.8 μL) of beads was transferred into 1-Step Human Coupled IVT reactions (25 μL) and cell-free EGFP translation was compared by native fluorescence in SDS-PAGE gels (FIG. 5). EGFP fluorescence was imaged (in-gel) using a 488 nm Typhoon variable-mode Imager. FIG. 5 demonstrates that fluorescent EGFP was effectively produced from the RCA product DNA generated from the DNA mini-circle when captured onto the streptavidin beads by biotin-streptavidin coupling at an estimated template concentration of 5 ng per microliter of IVTT reaction mixture. Biotinylated RCA product DNA was effectively coupled onto the streptavidin beads without any requirement of intermediate purification. As expected, little to no cell-free EGFP expression was observed using beads incubated with non-biotinylated AT primer. The use of MICROCON filters to remove excess hexamer primer contributed to higher non-specific expression (see, lane 3, FIG. 5) compared to the crude preparation process (see, lane 2, FIG. 5). For control purposes, TurboGFP was synthesized from 1 microgram of pCFE-GFP plasmid DNA (per kit manufacturer instructions) to compare relative fluorescence output.

TABLE 3

Quantitative estimation of RCA product DNA bead preparation prior to cell-free expression

| RCA reaction Primer | Clean-up | RCA product DNA concentration (ng/μL) | Volume (μL) used for 100 μL bead capture | Ratio of DNA (ng) to beads (μL) during capture |
|---|---|---|---|---|
| AT hexamer | none | 547.8 | 9.13 | 50 ng/bead μL |
| Biotinylated hexamer | none | 344.6 | 6.96 | 24 ng/bead μL |
|  |  |  | 14.51 | 50 ng/bead μL |
| AT hexamer | MICROCON | 81.6 | 61.27 | 50 ng/bead μL |
| Biotinylated hexamer | MICROCON | 127.2 | 18.94 | 24 ng/bead μL |
|  |  |  | 39.31 | 50 ng/bead μL |

The foregoing examples are illustrative of some features of the invention, and are selected embodiments from a manifold of all possible embodiments. The invention may be embodied in other specific forms without departing from the spirit or essential characteristics thereof. While only certain features of the invention have been illustrated, and described herein, one skilled in the art, given the benefit of this disclosure, will be able to make modifications/changes to optimize the parameters. The foregoing embodiments are therefore to be considered in all respects as illustrative rather than limiting on the invention described herein. Where necessary, ranges have been supplied, and those ranges are inclusive of all sub-ranges there between.

The invention claimed is:

1. A method for in vitro transcription and translation, comprising:
   contacting a purified double-stranded concatemeric DNA with a eukaryotic cell-free expression system, wherein the double-stranded concatemeric DNA comprises a plurality of tandem repeat sequences, and wherein each of the plurality of tandem repeat sequences comprises an expression sequence comprising a promoter, a cap-independent translation element (CITE), and an open reading frame; and
   expressing a protein in vitro from the double-stranded concatemeric DNA in the eukaryotic cell-free expression system,
   wherein a concentration of the double-stranded concatemeric DNA in the eukaryotic cell-free expression system is in a range from about 0.1 ng/µL to about 35 ng/µL.

2. The method of claim 1, wherein the concentration of the double-stranded concatemeric DNA in the eukaryotic cell-free expression system is in a range from about 0.5 ng/µL to about 20 ng/µL.

3. The method of claim 1, wherein the concentration of the double-stranded concatemeric DNA in the eukaryotic cell-free expression system is in a range from about 2 ng/µL to about 10 ng/µL.

4. The method of claim 1, wherein the concentration of the double-stranded concatemeric DNA in the eukaryotic cell-free expression system is in a range from about 3 ng/µL to about 7 ng/µL.

5. The method of claim 1, wherein the cap-independent translation element(CITE) comprises an internal ribosome entry site (IRES), a translation enhancing element (TEE), or a combination thereof.

6. The method of claim 1, wherein the open reading frame comprises a codon-optimized sequence for enhancing translation.

7. The method of claim 1, wherein the open reading frame comprises a tag sequence for purification of the expressed protein, an amino-terminal peptide fusion sequence derived from an IRES for enhanced ribosome recognition, or a combination thereof.

8. The method of claim 1, wherein the expression sequence further comprises a polyA sequence, a transcriptional termination sequence, an insulator sequence, or a combination thereof.

9. The method of claim 1, further comprising immobilizing the double-stranded concatemeric DNA onto a substrate prior to contacting the double-stranded concatemeric DNA with the eukaryotic cell-free expression system.

10. The method of claim 9, further comprising recovering the substrate-immobilized double-stranded concatemeric DNA from the eukaryotic cell-free expression system after expressing the protein in vitro and re-using the recovered substrate immobilized double-stranded concatemeric DNA for a subsequent in vitro transcription and translation reaction.

11. The method of claim 1, wherein the double-stranded concatemeric DNA is a rolling circle amplification (RCA) product DNA.

12. The method of claim 1, wherein the double-stranded concatemeric DNA comprises a biotinylated nucleotide, a phosphorothioated nucleotide, an inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide or a combination thereof.

13. A method for in vitro transcription and translation, comprising:
   providing a DNA mini-circle,
   generating a double-stranded concatemeric DNA via rolling circle amplification of the DNA mini-circle;
   purifying the generated double-stranded concatemeric DNA; and
   contacting the purified double-stranded concatemeric DNA with a eukaryotic cell-free expression system in vitro to express a protein from the double-stranded concatemeric DNA via transcription and translation,
   wherein a concentration of the double-stranded concatemeric DNA in the eukaryotic cell-free expression system is in a range from about 0.1 ng/µL to 35 ng/µL.

14. The method of claim 13, wherein the DNA mini-circle consists essentially of a minimalistic expression sequence consisting essentially of a promoter, a cap-independent translation element, and an open reading frame.

15. The method of claim 14, wherein the minimalistic expression sequence is devoid of any extraneous sequences that are required for propagation of a plasmid in a host cell.

16. The method of claim 14, wherein the cap-independent translation element (CITE) comprises an internal ribosome entry site (RES), a translation enhancing element (TEE), or a combination thereof.

17. The method of claim 14, wherein the minimalistic expression sequence further consists essentially of an insulator sequence, a polyA sequence, a transcriptional termination sequence, or a combination thereof.

18. The method of claim 14, wherein the open reading frame comprises a codon-optimized sequence for enhancing translation, a tag sequence for purification of the expressed protein, an amino-terminal peptide fusion sequence derived from an IRES for enhanced ribosome recognition, or a combination thereof.

19. The method of claim 13, wherein the concentration of the double-stranded concatemeric DNA in the eukaryotic cell-free expression system is in a range from about 0.5 to 20 ng/µL.

20. The method of claim 13, wherein the concentration of the double-stranded concatemeric DNA in the eukaryotic cell-free expression system is in a range from about 3 ng/µL to about 7 ng/µL.

21. The method of claim 13, wherein the double-stranded concatemeric DNA comprises a modified nucleotide, a nucleotide analogue, or a combination thereof.

22. The method of claim 13, wherein the double-stranded concatemeric DNA comprises a phosphorothioated nucleotide, a biotinylated nucleotide, an inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide or a combination thereof.

23. The method of claim 13, further comprising immobilizing the double-stranded concatemeric DNA onto a substrate prior to containing the double-stranded concatemeric DNA with the eukaryotic cell-free expression system.

24. The method of claim 23, further comprising recovering the substrate-immobilized double-stranded concatemeric DNA from the eukaryotic cell-free expression system after expressing the protein in vitro; and re-using the recovered substrate immobilized double-stranded concatemeric DNA for a subsequent in vitro transcription and translation reaction.

25. The method of claim 13, wherein the rolling circle amplification is performed using a final concentration of deoxyribonucleotide triphosphates (dNTPs), and optional alpha-thio dNTPs, in a range from about 10 µM to about 10 mM.

26. The method of claim 13, wherein the rolling circle amplification is performed using a random primer mixture comprising a nucleotide analogue.

27. The method of claim 26, wherein the random primer mixture has a sequence +N+N(atN)(atN)(atN)*N (SEQ ID NO:6) or 5'-biotin-NNNN*N*N (SEQ ID NO: 7).

* * * * *